(12) United States Patent
Bingel et al.

(10) Patent No.: US 6,620,953 B1
(45) Date of Patent: Sep. 16, 2003

(54) METHOD FOR PRODUCING MONOARYLOXY-ANSA-METALLOCENES

(75) Inventors: Carsten Bingel, Kriftel (DE); Hans-Herbert Brintzinger, Tägerwilen (CH); Hans-Robert-Hellmuth Damrau, Konstanz (DE)

(73) Assignee: Bassell Polyolefine GmbH, Wesseling (DE)

( * ) Notice: Subject to any disclaimer, the term of this patent is extended or adjusted under 35 U.S.C. 154(b) by 0 days.

(21) Appl. No.: 09/856,041

(22) PCT Filed: Nov. 18, 1999

(86) PCT No.: PCT/EP99/08854

§ 371 (c)(1),
(2), (4) Date: May 17, 2001

(87) PCT Pub. No.: WO00/31091

PCT Pub. Date: Jun. 2, 2000

(30) Foreign Application Priority Data

Nov. 25, 1998 (DE) ......................... 198 54 350
Mar. 19, 1999 (DE) ......................... 199 12 576

(51) Int. Cl.$^7$ .................. C07F 17/00; C07F 9/00; B01J 31/00; C08F 4/44
(52) U.S. Cl. .................. 556/11; 556/12; 556/43; 556/53; 526/127; 526/160; 526/943; 502/103; 502/117
(58) Field of Search .............. 556/11, 12, 43, 556/53; 502/103, 117; 526/127, 160, 943

(56) References Cited

U.S. PATENT DOCUMENTS

| | | | |
|---|---|---|---|
| 4,752,597 A | 6/1988 | Turner | 502/104 |
| 5,017,714 A | 5/1991 | Welborn, Jr. | 556/12 |
| 5,103,030 A | 4/1992 | Rohrmann et al. | 356/12 |
| 5,145,819 A | 9/1992 | Winter et al. | 502/117 |
| 5,304,614 A | 4/1994 | Winter et al. | 326/127 |
| 5,455,366 A | 10/1995 | Rohrmann et al. | 556/8 |
| 5,543,535 A | 8/1996 | Lisowsky | 556/11 |
| 5,556,997 A | 9/1996 | Strickler et al. | 556/11 |
| 5,597,935 A | 1/1997 | Jordan et al. | 556/11 |
| 5,612,462 A | 3/1997 | Lisowsky | 534/15 |
| 5,770,752 A | 6/1998 | Kaufmann et al. | 556/11 |
| 5,770,753 A | 6/1998 | Küber et al. | 556/11 |
| 5,786,432 A | 7/1998 | Küber et al. | 526/127 |
| 5,830,821 A | 11/1998 | Rohrmann et al. | 502/117 |
| 5,840,644 A | 11/1998 | Küber et al. | 502/117 |

FOREIGN PATENT DOCUMENTS

| | | |
|---|---|---|
| DE | 195 47147 | 7/1996 |
| DE | 195 47278 | 6/1997 |
| EP | 129 368 | 12/1984 |
| EP | 320 762 | 6/1989 |
| EP | 416 815 | 3/1991 |
| EP | 485 823 | 5/1992 |
| EP | 537 686 | 4/1993 |
| EP | 549 899 | 7/1993 |
| EP | 549 900 | 7/1993 |
| EP | 576 970 | 1/1994 |
| EP | 669 340 | 8/1995 |
| WO | 98/40331 | 9/1998 |

OTHER PUBLICATIONS

Repo et al., Journal of Organometallic Chemistry, vol. 541, pp. 363–366 (1997).*

(List continued on next page.)

Primary Examiner—Porfirio Nazario-Gonzalez
(74) Attorney, Agent, or Firm—Keil & Weinkauf

(57) ABSTRACT

The present invention relates to a process for preparing monoaryloxy-metallocenes of the formula (II), which comprises reacting a ligand starting compound of the formula (III) with a transition metal compound of the formula (I),

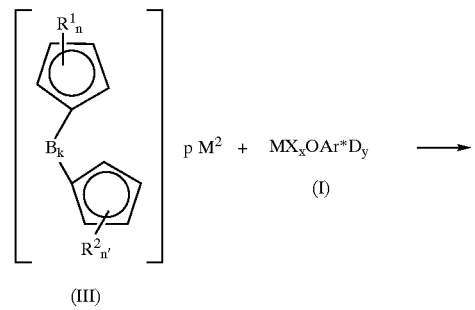

where the symbols are as defined in the claims.

One specific embodiment relates to the stereoselective preparation of monoaryloxy-metallocenes using a transition metal compound of the formula (Ia)

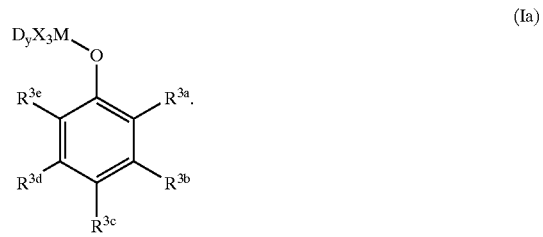

14 Claims, No Drawings

OTHER PUBLICATIONS

Chem. Rev.1992,92,965–944,Synthesis and Applications of Chiral Cyclopentadienylmetal Complexes, Halterman.

Angew.Chem.1995,107,1255–1283;Brintzinger et al. Stereospezifische Olefinpolymerisation mit chiralen Metallocenkatalysatoren.

J.Org.Chem.,232(1982)233–247 Wild et al. ansa–Metallocene Derivatives.

Organometallics1996,15,4030–4037;Diamone et al. Synthesis of Group 4 Metal rac–(EBI) . . . .

Chem, Abst, XP–002128402, p. 862, vol. 117 (1992).

J.Org.Chem.165(1979)319–327; Dormond et al.

J.Org.Chem.1977, 125(1), 63–69;Dormond et al.

J.Org.Chem.1975,101(1),71–84; Dormond et al.

* cited by examiner

METHOD FOR PRODUCING MONOARYLOXY-ANSA-METALLOCENES

The present invention relates to a stereoselective process for preparing monoaryloxy-ansa-metallocenes and to their use in the polymerization of olefins.

Metallocenes can, possibly in combination with one or more cocatalysts, be used as catalyst components for the polymerization and copolymerization of olefins. In particular, halogen-containing metallocenes are used as catalyst precursors which can, for example, be converted into a polymerization-active cationic metallocene complex by means of an aluminoxane(EP-A-129368).

Metallocenes are of great interest not only for the polymerization of olefins, but they can also be used as hydrogenation, epoxidation, isomerization and C—C coupling catalysts (Chem. Rev., 92 (1992), 965–994).

The preparation of metallocenes is known per se (U.S. Pat. No. 4,752,597; U.S. Pat. No. 5,017,714; EP-A-320762; EP-A-416815; EP-A-537686; EP-A-669340; H. H. Brintzinger et al., Angew. Chem., 107 (1995), 1255; H. H. Brintzinger et al., J. Organomet. Chem. 232 (1982), 233). For this purpose, for example, cyclopentadienyl-metal compounds can be reacted with halides of transition metals such as titanium, zirconium, hafnium, vanadium, niobium, tantalum, chromium, molybdenum, cerium and thorium.

It is also known from the literature that metallocenes can be obtained, for example, by reaction of cyclopentadienes with amides of elements of group 4 of the Periodic Table of the Elements (U.S. Pat. No. 5,597,935; R. F. Jordan et al., Organometallics, 15 (1996), 4030).

For the preparation of isotactic polypropylene (i-PP), use is generally made of ansa-metallocene halides in their racemic form. Substituted racemic ansa-bisindenylzirconium dichlorides have been found to give particularly good results and are therefore industrially important (EP 0485823, EP 0549900, EP 0576970, WO 98/40331). These industrially interesting metallocene dichlorides are predominantly sparingly soluble compounds, which makes, for example, the purification of these racemic metallocenes by recrystallization very difficult.

In their preparation, the desired substituted racemic ansa-bisindenyl-metallocene dichlorides are generally obtained together with the meso forms as 1:1 rac/meso diastereomer mixtures, as a result of which the yields of the desired rac-metallocenes based on the valuable ligand starting compounds are greatly restricted. The crude products formed in the preparation further comprise, in addition to the diastereomer mixtures, additional inorganic by-products (e.g. salts) and organic by-products (e.g. unreacted substituted cyclopentadienyl ligands). When metallocenes are used as catalyst components, in both homogeneous and heterogeneous catalyst systems, the by-products, in particular the meso form of the metallocene, adversely affect the catalyst activity in olefin polymerization and the specification of the polymer (for example, excessively high contents of extractables in the i-PP). Various methods are known for separating off the various by-products (U.S. Pat. No. 5,455,366, EP-A-0576970, DE-A-19547247, DE-A-19547248, U.S. Pat. No. 5,556,997).

Dormond et al., J. Organomet. Chem., vol. 101 (1), (1975) pp. 71–84 described chiral, phenoxy-substituted ansa-titanocenes.

Owing to the above-described rac/meso problems and the complicated purification, the costs of preparing the ansa-metallocene catalyst component are not yet in a desirable range.

It is an object of the present invention to find a more economical process for preparing readily purifiable racemic metallocenes, which is suitable, in particular, for preparing racemic, substituted ansa-bisindenyl-metallocenes which can be used directly as catalyst components in the polymerization of propylene.

We have found that this object is achieved by the use of specific transition metal compounds of the formula (I) for preparing metallocenes of the formula (II).

The present invention accordingly provides a process for preparing readily soluble and easily purifiable monoaryloxy-metallocenes of the formula (II), which comprises reacting a ligand starting compound (III) with a transition metal compound of the formula (I),

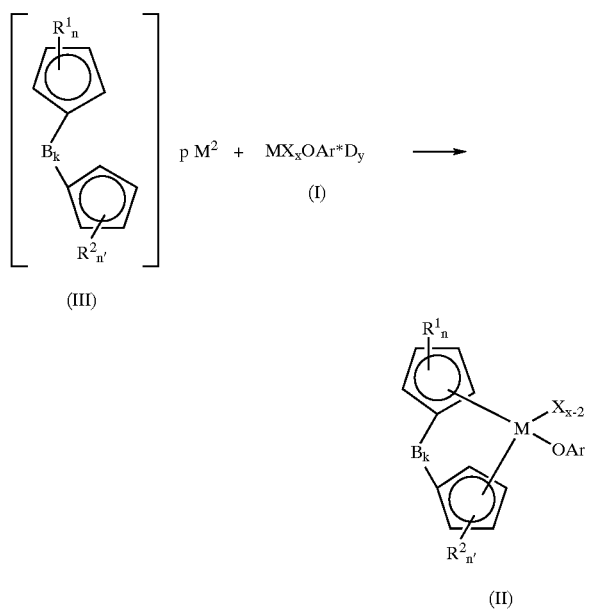

where

M is a metal of transition group III, IV, V or VI of the Periodic Table of the Elements, in particular Ti, Zr or Hf, particularly preferably zirconium, X is a halogen atom, in particular chlorine, Ar is a $C_6$–$C_{40}$ aromatic group, preferably $C_6$–$C_{24}$-aryl, $C_5$–$C_{24}$-heteroaryl such as pyridyl, furyl or quinolyl, $C_7$–$C_{30}$-alkylaryl, fluorinated $C_6$–$C_{24}$-aryl or fluorinated $C_7$–$C_{30}$-alkylaryl, particularly preferably a $C_6$–$C_{14}$-aryl group substituted by $C_1$–$C_6$-alkyl and/or $C_6$–$C_{10}$-Aryl radicals, D is an uncharged Lewis base ligand, preferably a linear, cyclic or branched oxygen-, sulfur-, nitrogen- or phosphorus-containing hydrocarbon, particularly preferably an ether, polyether, amine or polyamine, $M^2$ is Li, Na, K, MgCl, MgBr, Mg or Ca, $R^1$ are identical or different and are each $Si(R^{12})_3$, where $R^{12}$ are identical or different and are each a hydrogen atom or a $C_1$–$C_{40}$ group, preferably $C_1$–$C_{20}$-alkyl, $C_1$–$C_{10}$-fluoroalkyl, $C_1$–$C_{10}$-alkoxy, $C_6$–$C_{20}$-aryl, $C_6$–$C_{10}$-fluoroaryl, $C_6$–$C_{10}$-aryloxy, $C_2$–$C_{10}$-alkenyl, $C_7$–$C_{40}$-arylalkyl, $C_7$–$C_{40}$-alkylaryl or $C_8$–$C_{40}$-arylalkenyl, or $R^1$ is a $C_1$–$C_{30}$ group, preferably $C_1$–$C_{25}$-alkyl such as methyl, ethyl, tert-butyl, cyclohexyl or octyl, $C_2$–$C_{25}$-alkenyl, $C_3$–$C_{15}$-alkylalkenyl, $C_6$–$C_{24}$-aryl, $C_5$–$C_{24}$-heteroaryl, $C_7$–$C_{30}$-arylalkyl, $C_7$–$C_{30}$- alkylaryl, fluorinated $C_1$–$C_{25}$-alkyl, fluorinated $C_6$–$C_{24}$-aryl, fluorinated $C_7$–$C_{30}$-arylalkyl or fluorinated $C_7$–$C_{30}$-alkylaryl, or two or more radicals $R^1$ are joined to one another so that the radicals $R^1$ and the atoms of the cyclopentadienyl ring which connect them form a $C_4$–$C_{24}$ ring system which may be substituted, $R^2$ are identical or different and are each $Si(R^{12})_3$, where $R^{12}$ are identical or different and are each a hydrogen atom or a $C_1$–$C_{40}$ group, preferably $C_1$–$C_{20}$-alkyl, $C_1$–$C_{10}$-fluoroalkyl, $C_1$–$C_{10}$-alkoxy, $C_6$–$C_{14}$-aryl, $C_6$–$C_{10}$-fluoroaryl, $C_6$–$C_{10}$-aryloxy, $C_2$–$C_{10}$-alkenyl, $C_7$–$C_{40}$-arylalkyl, $C_7$–$C_{40}$-alkylaryl or $C_8$–$C_{40}$-arylalkenyl, or $R^2$ is a $C_1$–$C_{30}$ group, preferably $C_1$–$C_{25}$-alkyl such as methyl, ethyl, tert-butyl, cyclohexyl or octyl, $C_2$–$C_{25}$-alkenyl, $C_3$–$C_{15}$-alkylalkenyl, $C_6$–$C_{24}$-aryl, $C_5$–$C_{24}$-heteroaryl, $C_7$–$C_{30}$-arylalkyl, $C_7$–$C_{30}$-alkylaryl, fluorinated $C_1$–$C_{25}$-alkyl, fluorinated $C_6$–$C_{24}$-aryl, fluorinated $C_7$–$C_{30}$-arylalkyl or fluorinated $C_7$–$C_{30}$-alkylaryl, or two or more radicals $R^2$ are joined to one another so that the radicals $R^2$ and the atoms of the cyclopentadienyl ring which connect them form a $C_4$–$C_{24}$ ring system which may in turn be substituted, x is equal to the oxidation number of M minus 1, n is from 1 to 5 when k=0, and n is from 0 to 4 when k=1, n' is from 1 to 5 when k=0, and n, is from 0 to 4 when k=1, k is zero or 1 and, where the metallocene is unbridged when k=0 and the metallocene is bridged when k=1, with preference being given to k=1, and p is 1 for doubly positively charged metal ions or 2 for singly positively charged metal ions or metal ion fragments, y is from 0 to 2, B is a bridging structural element between the two cyclopentadienyl rings.

Examples of B are $M^3R^{13}R^{14}$ groups, where $M^3$ is carbon, silicon, germanium or tin and $R^{13}$ and $R^{14}$ are identical or different and are each a $C_1$–$C_{20}$-hydrocarbon-containing group such as $C_1$–$C_{10}$-alkyl, $C_6$–$C_{14}$-aryl or trimethylsilyl. B is preferably $CH_2$, $CH_2CH_2$, $CH(CH_3)CH_2$, $CH(C_4H_9)C(CH_3)_2$, $C(CH_3)_2$, $(CH_3)_2Si$, $(CH_3)_2Ge$, $(CH_3)_2Sn$, $(C_6H_5)_2Si$, $(C_6H_5)(CH_3)Si$, $Si(CH_3)(SiR^{20}R^{21}R^{22})$, $(C_6H_5)_2Ge$, $(C_6H_5)_2Sn$, $(CH_2)_4Si$, $CH_2Si(CH_3)_2$, o-$C_6H_4$ or 2,2'-$(C_6H_4)_2$, where $R^{20}$, $R^{21}$, $R^{22}$ are identical or different and are each a $C_1$–$C_{20}$-hydrocarbon-containing group such as $C_1$–$C_{10}$-alkyl or $C_6$–$C_{14}$-aryl. It is also possible for B together with one or more radicals $R^1$ and/or $R^2$ to form a monocyclic or polycyclic ring system.

The process of the present invention is preferably employed for preparing bridged metallocene compounds of the formula (II) in which k is 1 and one or both of the cyclopentadienyl rings is/are substituted so as to form an indenyl ring. The indenyl ring is preferably substituted, in particular in the 2 position, 4 position, 2,4,5 positions, 2,4,6 positions, 2,4,7 positions or 2,4,5,6 positions, by $C_1$–$C_{20}$ groups such as $C_1$–$C_{18}$-alkyl or $C_6$–$C_{18}$-aryl, where two or more substituents of the indenyl ring may also together form a ring system.

The invention further provides a process for preparing, in particular stereoselectively, readily soluble ansa-monoaryloxy-bisindenyl-metallocenes of the formula (VI), in which a ligand starting compound (V) is reacted with a transition metal compound of the formula (Ia),

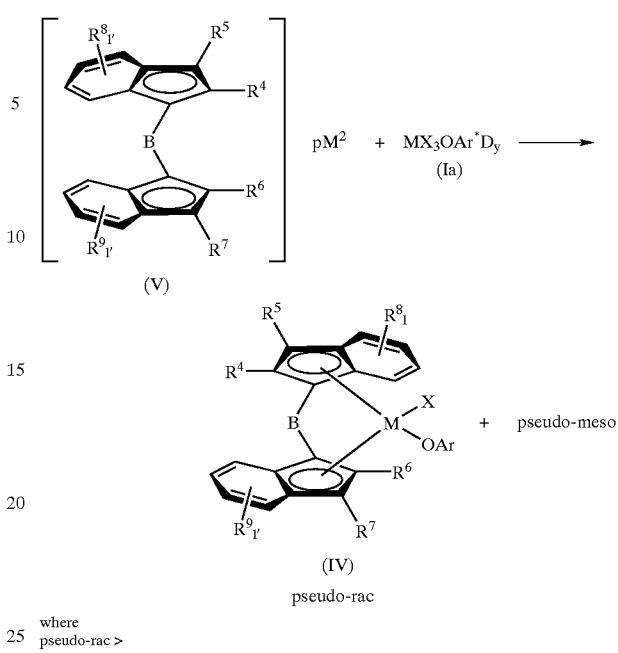

where
M is Ti, Zr or Hf, particularly preferably zirconium,
X is a halogen atom, in particular chlorine
Ar is a $C_6$–$C_{40}$ aromatic group, preferably $C_6$–$C_{24}$-aryl, $C_5$–$C_{24}$-heteroaryl such as pyridyl, furyl, or quinolyl, $C_7$–$C_{30}$-alkylaryl, fluorinated $C_6$–$C_{24}$-aryl or fluorinated $C_7$–$C_{30}$-alkylaryl, particularly preferably a $C_6$–$C_{14}$-aryl group substituted by $C_1$–$C_6$-alkyl and/or $C_6$–$C_{10}$-aryl radicals,
D is an uncharged Lewis base ligand, preferably a linear, cyclic or branched oxygen-, sulfur-, nitrogen- or phosphorus-containing hydrocarbon, particularly preferably an ether, polyether, amine or polyamine,
$M^2$ is Li, Na, K, MgCl, MgBr, Mg or Ca,
$R^4$, $R^6$ are identical or different and are each a hydrogen atom or a $C_1$–$C_{20}$ group, preferably $C_1$–$C_{18}$-alkyl such as methyl, ethyl, isopropyl, n-butyl, isobutyl, cyclohexyl or octyl, $C_2$–$C_{10}$-alkenyl, $C_3$–$C_{15}$-alkylalkenyl, $C_6$–$C_{18}$-aryl, $C_5$–$C_{18}$-heteroaryl such as pyridyl, furyl or quinolyl, $C_7$–$C_{20}$-arylalkyl, $C_7$–$C_{20}$-alkylaryl, fluorinated $C_1$–$C_{12}$-alkyl, fluorinated C6–$C_{18}$-aryl, fluorinated $C_7$–$C_{20}$-arylalkyl or fluorinated $C_7$–$C_{20}$-alkylaryl,
$R^5$, $R^7$ are identical or different and are each a hydrogen atom or a $C_1$–$C_{20}$ group, preferably $C_1$–$C_{18}$-alkyl such as methyl, ethyl, n-butyl, cyclohexyl or octyl, $C_2$–$C_{10}$-alkenyl, $C_3$–$C_{15}$-alkylalkenyl, $C_6$–$C_{18}$-aryl, $C_5$–$C_{18}$-heteroaryl such as pyridyl, furyl or quinolyl, $C_7$–$C_{20}$-arylalkyl, $C_7$–$C_{20}$-alkylaryl, fluorinated $C_1$–$C_{12}$-alkyl, fluorinated C6–$C_{10}$-aryl, fluorinated $C_7$–$C_{20}$-arylalkyl or fluorinated $C_7$–$C_{20}$-alkylaryl,
$R^8$ and $R^9$ are identical or different and are each a hydrogen atom, a halogen atom or a $C_1$–$C_{20}$ group, preferably a linear or branched $C_1$–$C_{18}$-alkyl group such as methyl, ethyl, tert-butyl, cyclohexyl or octyl, $C_2$–$C_{10}$-alkenyl, $C_3$–$C_{15}$-alkylalkenyl, a substituted or unsubstituted $C_6$–$C_{18}$-aryl group, in particular phenyl, tolyl, xylyl, tert-butylphenyl, ethylphenyl, di-tert-butylphenyl, naphthyl, acenaphthyl, phenanthrenyl or anthracenyl, $C_5$–$C_{18}$-heteroaryl such as pyridyl, furyl or quinolyl, $C_7$–$C_{20}$-arylalkyl, C7–$C_{20}$-alkylaryl, fluorinated $C_1$–$C_{12}$-alkyl, fluorinated $C_6$–$C_{18}$-aryl, fluorinated $C_7$–$C_{20}$-arylalkyl or fluorinated $C_7$–$C_{20}$-alkylaryl, and two radicals $R^8$ or $R^9$ form a monocyclic or polycyclic ring system which may in turn be substituted, l, l' are identical or different and are each an integer from zero to 4, preferably 1 or 2, particularly preferably 1, p is 1 for doubly positively charged metal ions or 2 for singly positively charged metal ions or metal ion fragments, y is from 0 to 2 and B is a bridging structural element between the two indenyl radicals.

Examples of B are $M^3R^{13}R^{14}$ groups, where $M^3$ is carbon, silicon, germanium or tin, preferably carbon or silicon, and $R^{13}$ and $R^{14}$ are identical or different and are each hydrogen or a $C_1$–$C_{20}$-hydrocarbon-containing group such as $C_1$–$C_{10}$-alkyl, $C_6$–$C_{14}$-aryl or trimethylsilyl. B is preferably $CH_2$, $CH_2CH_2$, $CH(CH_3)CH_2$, $CH(C_4H_9)C(CH_3)_2$, $C(CH_3)_2$, $(CH_3)_2Si$, $(CH_3)_2Ge$, $(CH_3)_2Sn$, $(C_6H_5)_2C$, $(C_6H_5)_2Si$, $(C_6H_5)(CH_3)Si$, $Si(CH_3)(SiR^{20}R^{21}R^{22})$, $(C_{6H5})Ge$, $(C_6H_5)_2Sn$, $(CH_2)_4Si$, $CH_2Si(CH_3)_2$, o-$C_6H_4$ or 2,2'-$(C_6H_4)_2$, where $R^{20}$, $R^{21}$, $R^{22}$ are identical or different and are each a $C_1$–$C_{20}$-hydrocarbon-containing group such as $C_1$–$C_{10}$-alkyl or $C_6$–$C_{14}$-aryl.

Preference is given to a process for preparing, in particular stereoselectively, readily soluble ansa-monoaryloxy-bisindenyl-metallocenes of the formula (VI), in which a ligand starting compound (V) is reacted with a transition metal compound of the formula (Ia), where M is zirconium, X is chlorine, Ar is a $C_6$–$C_{30}$ aromatic group, preferably a $C_1$–$C_6$-alkyl- and/or $C_6$–$C_{10}$-aryl-substituted $C_6$–$C_{14}$-aryl group, $C_5$–$C_{13}$-heteroaryl such as pyridyl, furyl or quinolyl or fluorinated $C_6$–$C_{10}$-aryl, particularly preferably a $C_6$–$C_{10}$-aryl group which is substituted by a $C_1$–$C_{10}$ group, e.g. a $C_1$–$C_6$-alkyl and/or $C_6$–$C_{10}$-aryl group, in at least one of the two ortho positions relative to the oxygen, D is an uncharged Lewis base ligand, preferably an ether, polyether, amine or polyamine, for example diethyl ether, dibutyl ether, 1,2-dimethoxyethane, tetrahydrofuran or N,N,N',N'-tetramethylethylenediamine, $M^2$ is Li, Na, K, MgCl, MgBr, Mg or Ca, preferably Li, Na, Mg, $R^4$, $R^6$ are identical or different and are each a hydrogen atom or a $C_1$–$C_{12}$-alkyl group, preferably methyl, ethyl, isopropyl, n-butyl, isobutyl or octyl, particularly preferably methyl or ethyl, $R^5$, $R^7$ are hydrogen atoms, $R^8$ and $R^9$ are identical or different and are each a hydrogen atom, a halogen atom or a $C_1$–$C_{20}$ group, preferably a linear or branched $C_1$–$C_8$-alkyl group such as methyl, ethyl, tert-butyl, cyclohexyl or octyl, $C_2$–$C_6$-alkenyl, $C_3$–$C_6$-alkylalkenyl, a $C_6$–$C_{18}$-aryl group which may be substituted, in particular phenyl, tolyl, xylyl, tert-butylphenyl, ethylphenyl, di-tert-butylphenyl, naphthyl, acenaphthyl, phenanthrenyl or anthracenyl, $C_5$–$C_{18}$-heteroaryl such as pyridyl, furyl or quinolyl, $C_7$–$C_{12}$-arylalkyl, $C_7$–$C_{12}$-alkylaryl, fluorinated $C_1$–$C_8$-alkyl, fluorinated $C_6$–$C_{18}$-aryl, fluorinated $C_7$–$C_{12}$-arylalkyl or fluorinated $C_7$–$C_{12}$-alkylaryl, l, l' are identical or different and are each an integer from zero to 4, preferably 1 or 2, particularly preferably 1, p is 1 for doubly positively charged metal ions or 2 for singly positively charged metal ions or metal ion fragments, y is from 0 to 2, B is a bridging structural element between the two indenyl radicals and is preferably $(CH_3)_2Si$, $(CH_3)_2Ge$, $(C_6H_5)_2Si$, $CH_2CH_2$, $CH_2$, $C(CH_3)_2$, $(C_6H_5)_2C$, particularly preferably $(CH_3)_2Si$, $CH_2$ and $CH_2CH_2$.

The pseudo-rac form of the ansa-monoaryloxy-bisindenyl-metallocenes of the formula (IV) is formed preferentially over the corresponding pseudo-meso form when specifically substituted aryloxy radicals are used in the transition metal compound of the formula (Ia),

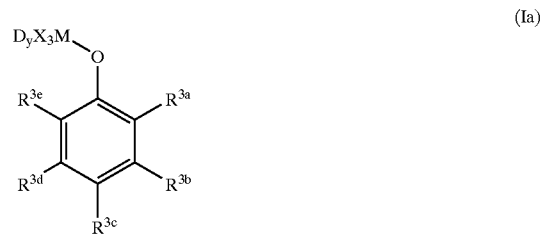

(Ia)

where

M is Ti, Zr or Hf, particularly preferably zirconium,

X is a halogen atom, in particular chlorine,

D is an uncharged Lewis base ligand, preferably a linear, cyclic or branched oxygen-, sulfur-, nitrogen- or phosphorus-containing hydrocarbon, particularly preferably an ether, polyether, amine or polyamine, $R^{3a}$ is halogen or $Si(R^{12})_3$, where $R^{12}$ are identical or different and are each a hydrogen atom or a $C_1$–$C_{14}$ group, preferably $C_1$–$C_4$-alkyl, $C_1$–$C_4$-alkoxy, $C_6$–$C_{10}$-aryl, $C_6$–$C_{10}$-fluoroaryl, $C_6$–$C_{10}$-aryloxy, $C_2$–$C_{10}$-alkenyl, $C_7$–$C_{14}$-arylalkyl or $C_7$–$C_{14}$-alkylaryl, or $R^{3a}$ is a $C_1$–$C_{30}$ group, preferably $C_1$–$C_{25}$-alkyl such as methyl, ethyl, isopropyl, tert-butyl, cyclohexyl or octyl, $C_2$–$C_{25}$-alkenyl, $C_3$–$C_{15}$-alkylalkenyl, $C_6$–$C_{24}$-aryl, $C_5$–$C_{24}$-heteroaryl, $C_1$–$C_{10}$-alkyloxy, $C_6$–$C_{10}$-aryloxy, $C_7$–$C_{30}$-arylalkyl, $C_7$–$C_{30}$-alkylaryl, fluorinated $C_1$–$C_{25}$-alkyl, fluorinated $C_6$–$C_{24}$-aryl, fluorinated $C_7$–$C_{30}$-arylalkyl or fluorinated $C_7$–$C_{30}$-alkylaryl, $R^{3b}$ to $R^{3e}$ are identical or different and are each hydrogen, halogen or a $C_1$–$C_{30}$ group, preferably $C_1$–$C_{25}$-alkyl such as methyl, ethyl, isopropyl, tert-butyl, cyclohexyl or octyl, $C_2$–$C_{25}$-alkenyl, $C_3$–$C_{15}$-alkylalkenyl, $C_6$–$C_{24}$-aryl, $C_5$–$C_{24}$-heteroaryl, $C_1$–$C_{10}$-alkyloxy, $C_6$–$C_{10}$-aryloxy, $C_7$–$C_{30}$-arylalkyl, $C_7$–$C_{30}$-alkylaryl, fluorinated $C_1$–$C_{25}$-alkyl, fluorinated $C_6$–$C_{24}$-aryl, fluorinated $C_7$–$C_{30}$-arylalkyl or fluorinated C7–$C_{30}$-alkylaryl, or two or more radicals $R^{3a}$ to $R^{3e}$ may be joined to one another so that the radicals $R^3$ and the atoms of the benzene ring which connect them form a $C_4$–$C_{24}$ ring system which may in turn be substituted, and y is from 0 to 2.

The preferred formation of the pseudo-rac form (IV) over the pseudo-meso form (IVa) (stereoselective reaction) means that the ratio of pseudo-rac/pseudo-meso in the crude metallocene product after the synthesis is greater than 1, preferably greater than 2, particularly preferably greater than 4 and very particularly preferably greater than 8.

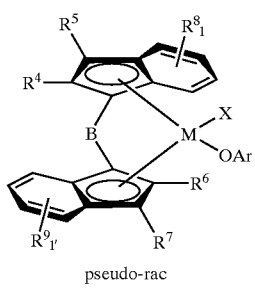

pseudo-rac (IV)

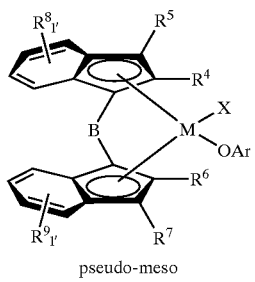

pseudo-meso (IVa)

In the stereoselective process for preparing compounds of the formula (IV), particular preference is given to using transition metal compounds of the formula (Ia) where M is zirconium, X is chlorine, D is an uncharged oxygen- or nitrogen-containing Lewis base ligand, preferably an ether, polyether, amine or polyamine, for example diethyl ether, dibutyl ether, 1,2-dimethoxyethane, tetrahydrofuran or N,N,N,N'-tetramethylethylenediamine, $R^{3a}$ is halogen or a $C_1$–$C_{10}$ group, preferably $C_1$–$C_8$-alkyl such as methyl, ethyl, isopropyl, tert-butyl, cyclohexyl or octyl, $C_2$–$C_8$-alkenyl, $C_3$–$C_8$-alkylalkenyl, $C_6$–$C_{10}$-aryl, $C_5$–$C_9$-heteroaryl, $C_1$–$C_4$-alkyloxy, $C_6$-aryloxy, $C_7$–$C_{10}$-arylalkyl, $C_7$–$C_{10}$-alkylaryl, $R^{3b}$ to $R^{3e}$ are identical or different and are each hydrogen, halogen or a $C_1$–$C_{10}$ group, preferably $C_1$–$C_8$-alkyl such as methyl, ethyl, isopropyl, tert-butyl, cyclohexyl or octyl, $C_2$–$C_8$-alkenyl, $C_3$–$C_8$-alkylalkenyl, $C_6$–$C_{10}$-aryl, $C_5$–$C_9$-heteroaryl, $C_1$–$C_4$-alkyloxy, $C_6$-aryloxy, $C_7$–$C_{10}$-arylalkyl, $C_7$–$C_{10}$-alkylaryl, or two or more radicals $R^{3a}$ to $R^{3e}$ may be joined to one another so that the radicals $R^3$ and the atoms of the benzene ring which connect them form a $C_4$–$C_8$ ring system which may in turn be substituted, and y is from 0 to 2.

In the stereoselective process for preparing compounds of the formula (IV), very particular preference is given to using transition metal compounds of the formula (Ia) where M is zirconium, X is chlorine, D is tetrahydrofuran, 1,2-dimethoxyethane or N,N,N',N'-tetramethylethylenediamine, $R^{3a}$ is chlorine, bromine or a $C_1$–$C_{10}$ group, preferably $C_1$–$C_6$-alkyl such as methyl, ethyl, isopropyl, tert-butyl or cyclohexyl, $C_2$–$C_4$-alkenyl, $C_6$–$C_{10}$-aryl, $R^{3b}$ to $R^{3d}$ are identical or different and are each hydrogen, chlorine, bromine or a $C_1$–$C_{10}$ group, preferably $C_1$–$C_6$-alkyl such as methyl, ethyl, isopropyl, tert-butyl or cyclohexyl, $C_2$–$C_4$-alkenyl, $C_6$–$C_{10}$-aryl, or two or more radicals $R^{3a}$ to $R^{3e}$ may be joined to one another so that the radicals $R^3$ and the atoms of the benzene ring which connect them form a $C_4$–$C_6$ ring system which may in turn be substituted, and y is from 0 to 2.

The synthesis of transition metal compounds of the formulae (I) and (Ia) is known in principle from the literature (M. Mitani et al., Polymer Bulletin 34 (1995), pages 199 to 202; H. Yasuda et al., J. Organomet. Chem. 493 (1994), pages 105 to 116).

The preparation can be carried out by one of the following two routes:

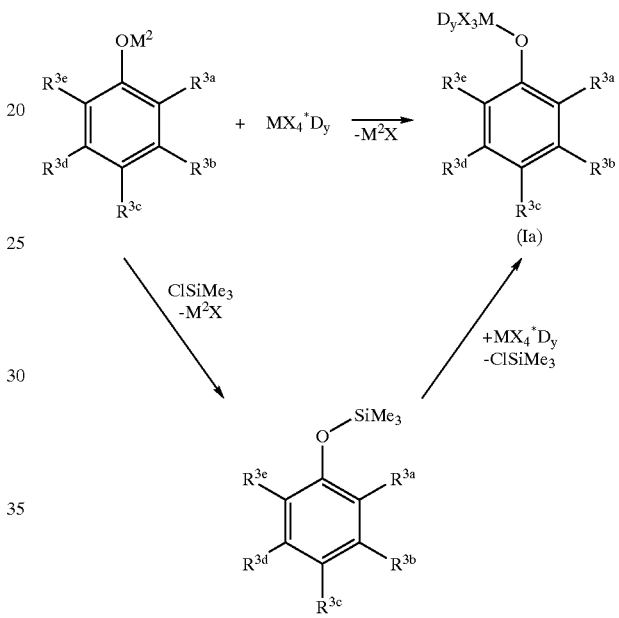

where the symbols and indices are as defined above.

In the first case, an aryloxy salt of an alkali metal or alkaline earth metal is reacted directly with a tetrahalide of a metal of transition group IV of the Periodic Table of the Elements, e.g. titanium, zirconium or hafnium tetrachloride, advantageously in the form of the bis-THF adduct, to give the compound (Ia).

In the second case, the aryloxy salt of the alkali metal or alkaline earth metal is firstly reacted with a silyl chloride such as trimethylsilyl chloride to form the silyl ether which, possibly after isolation, is then reacted with a tetrahalide of a metal of transition group IV of the Periodic Table of the Elements, e.g. titanium, zirconium or hafnium tetrachloride, advantageously in the form of the bis-THF adduct, to give the compound (Ia).

After separating off the salts formed ($M^2X$) and/or removing the substituted chlorosilane, the transition metal compounds of the formulae (I) and (Ia) can generally be obtained by crystallization.

The aryloxy salts of alkali metals or alkaline earth metals can be prepared by deprotonation of the corresponding hydroxyaromatic by means of a suitable base, for example butyllithium, methyllithium, sodium hydride, potassium hydride, sodium, potassium or Grignard compounds, in an inert solvent or solvent mixture.

Nonlimiting examples of suitable inert solvents are aliphatic or aromatic hydrocarbons such as benzene, toluene, xylene, mesitylene, ethylbenzene, chlorobenzene, dichlorobenzene, fluorobenzene, decalin, tetralin, pentane, hexane, cyclohexane, heptane, 1,2-dichloroethane, dichloromethane, ethers such as diethyl ether, di-n-butyl ether, tert-butyl methyl ether (MTBE), tetrahydrofuran (THF), 1,2-dimethoxyethane (DME), anisole, triglyme, dioxane and also any mixtures of these. Nonlimiting examples of solvent mixtures are toluene, hexane, heptane, xylene, tetrahydrofuran (THF), dimethoxyethane (DME), toluene/THF, heptane/DME and toluene/DME.

The reactions are carried out at from −78 to 150° C., preferably from 0 to 110° C.

Illustrative but nonrestrictive examples of hydroxyaromatics which can be used for preparing the transition metal compounds of the formula (I) and (Ia) for use in the process of the present invention are:

2,4-di-tert-butylphenol; 2,6-di-tert-butylphenol;

3,5-di-tert-butylphenol; 2,6-di-sec-butylphenol;

2,4-dimethylphenol; 2,3-dimethylphenol; 2,5-dimethylphenol;

2,6-dimethylphenol; 3,4-dimethylphenol; 3,5-dimethylphenol;

phenol; 2-methylphenol; 3-methylphenol; 4-methylphenol;

2-ethylphenol; 3-ethylphenol; 4-ethylphenol; 2-sec-butylphenol;

2-tert-butylphenol; 3-tert-butylphenol; 4-sec-butylphenol;

4-tert-butylphenol; 2-isopropyl-5-methylphenol;

4-isopropyl-3-methylphenol; 5-isopropyl-2-methylphenol;

5-isopropyl-3-methylphenol; 2,4-bis(2-methyl-2-butyl)phenol;

2,6-di-tert-butyl-4-methylphenol; 4-nonylphenol;

2-isopropylphenol; 3-isopropylphenol; 4-isopropylphenol;

2-propylphenol;

4-propylphenol; 2,3,5-trimethylphenol; 2,3,6-trimethylphenol;

2,4,6-trimethylphenol; 3,4,5-trimethylphenol;

2-tert-butyl-4-methylphenol; 2-tert-butyl-5-methylphenol;

2-tert-butyl-6-methylphenol; 4-(2-methyl-2-butyl)phenol;

2-tert-butyl-4-ethylphenol; 2,6-diisopropylphenol; 4-octylphenol;

4-(1,1,3,3-tetramethylbutyl)phenol;

2,6-di-tert-butyl-4-ethylphenol;

4-sec-butyl-2,6-di-tert-butylphenol; 4-dodecylphenol;

2,4,6-tri-tert-butylphenol; 3-(pentadecyl)phenol;

2-methyl-1-naphthol;

1-naphthol; 2-naphthol; 1-acenaphthenol; 2-hydroxybiphenyl;

3-hydroxybiphenyl; 4-hydroxybiphenyl; hydroxypyridines;

hydroxyquinolines; 2-hydroxycarbazole; hydroxyquinaldines;

8-hydroxyquinazoline; 2-hydroxyquinoxaline;

2-dihydroxybenzofuran;

2-hydroxydiphenylmethane, 1-hydroxyisoquinoline, 5,6,7,8-tetrahydro-1-naphthol.

In the process of the present invention for preparing metallocenes of the formulae (II) and (IV), the transition metal compounds of the formulae (I) and (Ia) can be used in isolated form or in the form of a solution or suspension as obtained after their preparation. The reactive by-products which interfere in the further reaction, e.g. trimethylchlorosilane, should be removed before the reaction with the substituted cyclopentadienyl anions.

Illustrative but not restrictive examples of transition metal compounds of the formula (Ia) which can be used for the preparation, in particular stereoselective preparation, of the metallocenes of the formula (IV) are:

Cl$_3$Zr(O-2,4-(tert-Bu)$_2$C$_6$H$_3$) (THF)$_2$, Cl$_3$Zr(O-2,6-(tert-Bu)$_2$C$_6$H$_3$)

(THF)$_2$, Cl$_3$Zr(O-3,5-(tert-Bu)$_2$C$_6$H$_3$) (THF)$_2$,

Cl$_3$Zr(O-2,6-Me$_2$C$_6$H$_3$) (THP)$_2$, Cl$_3$Zr(O-2,4-Me$_2$C$_6$H$_3$) (THF)$_2$,

Cl$_3$Zr(O-2,3-Me$_2$C$_6$H$_3$) (THF)$_2$, Cl$_3$Zr(O-3,5-Me$_2$C$_6$H$_3$) (THF)$_2$,

Cl$_3$Zr(O-2-Me-C$_6$H$_4$) (THF)$_2$, Cl$_3$Zr(O-2-Et-C$_6$H$_4$) (DME),

Cl$_3$Zr(O-2-isoprop-C$_6$H$_4$) (DME), Cl$_3$Zr(O-2-n-prop-C$_6$H$_4$) (THF)$_2$, Cl$_3$Zr(O-2-sec-Bu-C$_6$H$_4$) (DME), Cl$_3$Zr(O-2-tert-Bu-C$_6$H$_4$) (THF)$_2$, Cl$_3$Zr(O-2-isoprop-5-Me-C$_6$H$_3$) (THF)$_2$, Cl$_3$Zr(O-2,4,6-Me$_3$C$_6$H$_2$) (THF)$_2$, Cl$_3$Zr(O-2-tert-Bu-6-Me-C$_6$H$_3$) (DME), Cl$_3$Zr(O-2,6-(isoprop)$_2$—C$_6$H$_3$) (THF)$_2$, Cl$_3$Zr(O-(1-naphthyl)) (DME), Cl$_3$Zr(O-2-Ph-C$_6$H$_4$) (THF)$_2$.

The process of the present invention can in principle be used for preparing various types of metallocenes, for example bridged or unbridged biscyclopentadienyl complexes as are described, for example, in EP 129 368, EP 561 479, EP 545 304 and EP 576 970, monocyclopentadienyl complexes such as bridged amidocyclopentadienyl complexes described, for example, in EP 416 815, multinuclear cyclopentadienyl complexes as described in EP 632 063, n-ligand-substituted tetrahydropentalenes as described in EP 659 758 or n-ligand-substituted tetrahydroindenes as described in EP 661 300.

The process of the present invention is preferably employed for preparing metallocenes whose synthesis can give them as diastereomers, particularly preferably ansa-metallocenes of the formula (IV).

The ligand starting compounds (V) used in the process of the present invention for the stereoselective preparation of readily soluble monoaryloxy-bisindenyl-metallocenes of the formula (IV) are prepared by double deprotonation of the corresponding bisindenyl compound (Va) in an inert solvent or solvent mixture:

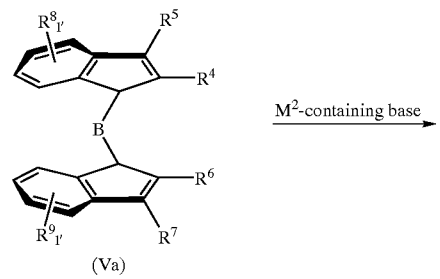

(Va)

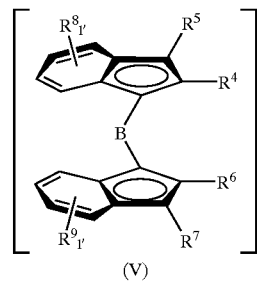

(V)

where the symbols and indices are as defined above.

Nonrestrictive examples of suitable bases are organolithium compounds such as n-butyllithium, sec-butyllithium, tert-butyllithium, methyllithium, organomagnesium compounds, alkali metals such as sodium, potassium, alkali metal hydrides such as sodium hydride, potassium hydride or alkali metal amides such as lithium amide, sodium amide, potassium amide, lithium hexamethyldisilazide, sodium hexamethyldisilazide, potassium hexamethyldisilazide, lithium diisopropylamide or lithium diethylamide.

Suitable inert solvents are aliphatic or aromatic hydrocarbons such as benzene, toluene, xylene, mesitylene, ethylbenzene, chlorobenzene, dichlorobenzene, fluorobenzene, decalin, tetralin, pentane, hexane, cyclohexane, heptane, 1,2-dichloroethane, dichloromethane, ethers such as diethyl ether, di-n-butyl ether, tert-butyl methyl ether (MTBE), tetrahydrofuran (THF), 1,2-dimethoxyethane (DME), anisole, triglyme, dioxane and any mixtures of these. Preference is given to solvents or solvent mixtures in which the subsequent reaction to form the metallocene complex of the formula (IV) can likewise be carried out directly. Nonrestrictive examples of such solvents are toluene, hexane, heptane, xylene, tetrahydrofuran (THF), dimethoxyethane (DME), toluene/THF, heptane/DME and toluene/DME.

The deprotonation of the bridged bisindenyl ligands of the formula (Va) is carried out at from −78 to 150° C., preferably from 0 to 110° C.

The molar ratio of the above-described suitable bases to the bridged bisindenyl ligands of the formula (Va) is generally in the range from 10 to 0.1, preferably from 4 to 0.5, particularly preferably from 3 to 0.8.

In the process of the present invention, it is possible to use bisindenyl ligands as are described in EP-A-0485823, EP-A-0549900, EP-A-0576970, WO 98/22486 and WO 98/40331 for preparing the corresponding metallocene dichlorides.

Illustrative but nonrestrictive examples of preferred bridged bisindenyl ligands of the formula (Va) for use in the process of the present invention for the stereoselective preparation of readily soluble ansa-monoaryloxy-bisindenyl-metallocenes of the formula (IV) are:

dimethylbis(2-methylindenyl)silane
1,1-bis(2-methylindenyl)methane
2,2-bis(2-methylindenyl)propane
dimethylbis(2-methylbenzoindenyl)silane
dimethylbis(4-naphthylindenyl)silane
dimethylbis(2-methyl-4-(1-naphthyl)indenyl)silane
1,1-bis(2-methyl-4-(1-naphthyl)indenyl)methane
2,2-bis(2-methyl-4-(1-naphthyl)indenyl)propane
dimethylbis(2-methyl-4-(2-naphthyl)indenyl)silane
dimethylbis(2-methyl-4-phenylindenyl)silane
1,1-bis(2-methyl-4-phenylindenyl)methane
2,2-bis(2-methyl-4-phenylindenyl)propane
dimethylbis(2-methyl-4-t-butylindenyl)silane
dimethylbis(2-methyl-4-isopropylindenyl)silane
dimethylbis(2-methyl-4-ethylindenyl)silane
dimethylbis(2,4-dimethylindenyl)silane
dimethylbis(2-ethylindenyl)silane
dimethylbis(2-ethyl-4-ethylindenyl)silane
dimethylbis(2-ethyl-4-phenylindenyl)silane
dimethylbis(2-methyl-4,5-benzoindenyl)silane
1,1-bis(2-methyl-4,5-benzoindenyl)methane
2,2-bis(2-methyl-4,5-benzoindenyl)propane
dimethylbis(2-methyl-4,6-diisopropylindenyl)silane
dimethylbis(2-methyl-4,5-diisopropylindenyl)silane
dimethylbis(2,4,6-trimethylindenyl)silane
dimethylbis(2,5,6-trimethylindenyl)silane
dimethylbis(2,4,7-trimethylindenyl)silane
dimethylbis(2-methyl-5-isobutylindenyl)silane
dimethylbis(2-methyl-5-t-butylindenyl)silane
methyl(phenyl)bis(2-methyl-4-phenylindenyl)silane
methyl(phenyl)bis(2-methyl-4,6-diisopropylindenyl)silane
methyl(phenyl)bis(2-methyl-4-isopropylindenyl)silane
methyl(phenyl)bis(2-methyl-4,5-benzoindenyl)silane
methyl(phenyl)bis(2-methyl-4,5-(methylbenzo)indenyl)silane
methyl(phenyl)bis(2-methyl-4,5-(tetramethylbenzo)indenyl)silane
methyl(phenyl)bis(2-methylindenyl)silane
methyl(phenyl)bis(2-methyl-5-isobutylindenyl)silane
1,2-bis(2-methyl-4-phenylindenyl)ethane
1,2-bis(2-methyl-4,6-diisopropylindenyl)ethane
1,2-bis(2-methyl-4,5-benzoindenyl)ethane
1,2-bis(2,4,7-trimethylindenyl)ethane
1,2-bis(2-methylindenyl)ethane
dimethylbis(2-methyl-4-(tert-butylphenylindenyl)silane
dimethylbis(2-methyl-4-(4-trifluoromethylphenylindenyl)silane
dimethylbis(2-methyl-4-(4-methoxyphenylindenyl)silane
dimethylbis(2-ethyl-4-(4-tert-butylphenylindenyl)silane
dimethylbis(2-ethyl-4-(4-methylphenylindenyl)silane
dimethylbis(2-ethyl-4-(4-ethylphenylindenyl)silane
dimethylbis(2-ethyl-4-(4-trifluoromethylphenylindenyl)silane
dimethylbis(2-ethyl-4-(4-methoxyphenylindenyl)silane
dimethylbis(2-methyl-4-(4'-tert-butylphenyl)indenyl)silane
dimethylbis(2-methyl-4-(3'5'-di-tert-butylphenyl)indenyl)silane
1,1-bis(2-methyl-4-(4'-tert-butylphenyl)indenyl)methane
2,2-bis(2-methyl-4-(4'-tert-butylphenyl)indenyl)propane
dimethylbis(2-methyl-4-(4'-methylphenyl)indenyl)silane
dimethylbis(2-methyl-4-(4'-ethylphenyl)indenyl)silane
dimethylbis(2-methyl-4-(4'-n-propylphenyl)indenyl)silane
dimethylbis(2-methyl-4-(4'-isopropylphenyl)indenyl)silane
dimethylbis(2-methyl-4-(4'-n-butylphenyl)indenyl)silane
dimethylbis(2-methyl-4-(4'-hexylphenyl)indenyl)silane dimethylbis(2-methyl-4-(4'-sec-butylphenyl)indenyl)
   silane
dimethylbis(2-ethyl-4-phenyl)indenyl)silane
dimethylbis(2-ethyl-4-(4'-methylphenyl)indenyl)silane
dimethylbis(2-ethyl-4-(4'-ethylphenyl)indenyl)silane
dimethylbis(2-ethyl-4-(4'-n-propylphenyl)indenyl)silane
dimethylbis(2-ethyl-4-(4'-isopropylphenyl)indenyl)silane
dimethylbis(2-ethyl-4-(4'-n-butylphenyl)indenyl)silane
dimethylbis(2-ethyl-4-(4'-hexylphenyl)indenyl)silane
dimethylbis(2-ethyl-4-(4'-pentylphenyl)indenyl)silane
dimethylbis(2-ethyl-4-(4'-cyclohexylphenyl)indenyl)
   silane
dimethylbis(2-ethyl-4-(4'-sec-butylphenyl)indenyl)silane
dimethylbis(2-ethyl-4-(4'-tert-butylphenyl)indenyl)silane
dimethylbis(2-ethyl-4-(3'5'-di-tert-butylphenyl)indenyl)
   silane
1,1-bis(2-ethyl-4-(4'-tert-butylphenyl)indenyl)methane
2,2-bis(2-ethyl-4-(4'-tert-butylphenyl)indenyl)propane
dimethylbis(2-n-propyl-4-phenyl)indenyl)silane
dimethylbis(2-n-propyl-4-(4'-methylphenyl)indenyl)
   silane
dimethylbis(2-n-propyl-4-(4'-ethylphenyl)indenyl)silane
dimethylbis(2-n-propyl-4-(4'-n-propylphenyl)indenyl)
   silane
dimethylbis(2-n-propyl-4-(4'-isopropylphenyl)indenyl)
   silane
dimethylbis(2-n-propyl-4-(4'-n-butylphenyl)indenyl)
   silane
dimethylbis(2-n-propyl-4-(4'-hexylphenyl)indenyl)silane
dimethylbis(2-n-propyl-4-(4'-cyclohexylphenyl)indenyl)
   silane
dimethylbis(2-n-propyl-4-(4'-sec-butylphenyl)indenyl)
   silane
dimethylbis(2-n-propyl-4-(4'-tert-butylphenyl)indenyl)
   silane
dimethylbis(2-n-propyl-4-(3'5'-di-tert-butylphenyl)
   indenyl)silane
1,1-bis(2-n-propyl-4-(4'-tert-butylphenyl)indenyl)
   methane
2,2-bis(2-n-propyl-4-(4'-tert-butylphenyl)indenyl)
   propane
dimethylbis(2-isopropyl-4-4-phenyl)indenyl)silane
dimethylbis(2-isopropyl-4-(4'-methylphenyl)indenyl)
   silane
dimethylbis(2-isopropyl-4-(41'-ethylphenyl)indenyl)
   silane
dimethylbis(2-isopropyl-4-(4'n-propylphenyl)indenyl)
   silane
dimethylbis(2-isopropyl-4-(4'-isopropylphenyl)indenyl)
   silane
dimethylbis(2-isopropyl-4-(4'-n-butoylphenyl)indenyl)
   silane
dimethylbis(2-isopropyl-4-(4'-hexylphenyl)indenyl)
   silane
dimethylbis(2-isopropyl-4-(4'-cyclohexylphenyl)indenyl)
   silane
dimethylbis(2-isopropyl-4-(4'-sec-butylphenyl)indenyl)
   silane
dimethylbis(2-isopropyl-4-(4'-tert-butylphenyl)indenyl)
   silane
1,1-bis(2-isopropyl-4-(4'-tert-butylphenyl)indenyl)
   methane
dimethylbis(2-n-butyl-4-phenyl)indenyl)silane
dimethylbis(2-n-butyl-4-(4'-methylpheny)indenyl)silane
dimethylbis(2-n-butyl-4-(4'-ethylphenyl)indenyl)silane
dimethylbis(2-n-butyl-4-(4'-n-propylphenyl)indenyl)
   silane
dimethylbis(2-n-butyl-4-(4'-isopropylphenyl)indenyl)
   silane
dimethylbis(2-n-butyl-4-(4'-n-butylphenyl)indenyl)silane
dimethylbis(2-n-butyl-4-(4'-hexylphenyl)indenyl)silane
dimethylbis(2-n-butyl-4-(4'-cyclohexylphenyl)indenyl)
   silane
dimethylbis(2-n-butyl-4-(4'-sec-butylphenyl)indenyl)
   silane
dimethylbis(2-n-butyl-4-(4'-tert-butylphenyl)indenyl)
   silane
dimethylbis(2-(2-methylpropyl)-4-phenyl)indenyl)silane
dimethylbis(2-(2-methylpropyl)-4-(4'-methylphenyl)
   indenyl)silane
dimethylbis(2-(2-methylpropyl)-4-(4'-ethylphenyl)
   indenyl)silane
dimethylbis(2-(2-methylpropyl)-4-(4'-n-propylphenyl)
   indenyl)silane
dimethylbis(2-(2-methylpropyl)-4-(4'-isopropylphenyl)
   indenyl)silane
dimethylbis(2-(2-methylpropyl)-4-(4'-n-butylphenyl)
   indenyl)silane
dimethylbis(2-(2-methylpropyl)-4-(4'-(2-methylpropyl)
   phenyl)indenyl)silane
dimethylbis(2-(2-methylpropyl)-4-(4'-cyclo(2-
   methylpropyl)phenyl)indenyl)silane
dimethylbis(2-(2-methylpropyl)-4-(4'-sec-butylphenyl)
   indenyl)silane
dimethylbis(2-(2-methylpropyl)-4-(4'-tert-butylphenyl)
   indenyl)silane
dimethylbis(2-ethyl-4-(4'-tert-butylphenyl)indenyl)
   germane
dimethylbis(2-methyl-4-(4'-tert-butylphenyl)indenyl)
   germane
1,2-bis(2-methyl-4-(4'-tert-butylphenyl)indenyl)ethane
1,2-bis(2-ethyl-4-phenyl)indenyl)ethane
1,2-bis(2-ethyl-4-(4'-tert-butylphenyl)indenyl)ethane
1,2-bis(2-n-propyl-4-phenyl)indenyl)ethane
1,2-bis(2-n-propyl-4-(4'-tert-butylphenyl)indenyl)ethane
1,2-bis(2-isopropyl-4-(4-phenyl)indenyl)ethane
1,2-bis(2-isopropyl-4-(4'-tert-butylphenyl)indenyl)ethane
1,2-bis(2-(2-methypropyl-)4-(4-phenyl)pindenyl)ethane
1,2-bis(2-(2-methylpropyl)-4-(4'-tert-butylphenyl)
   indenyl)ethane
1-methyl-1,2-bis(2-ethyl-4-(4'-tert-butylphenyl)indenyl)
   ethane
dimethyl-(12-methylazapentalene)(2-methylindenyl)
   isilane
dimethyl(2-methylazapentalene)(2-methyl-4-
   phenylindenyl)sisane
dimethyl(2-methylazapentalene)(2-methyl-4,5-
   benzoindenyl)silane
dimethyl(2-methylazapentalene)(2-ethyl-4-(4'-tert-butyl-
   phenyl)indenyl)silane dimethyl(2-methylazapentalene)(2-methyl-4-(4'-tert-butylphenyl)indenyl)silane dimethyl(2-methylazapentalene)(2-n-propyl-4-(4'-tert-butyl-phenyl)indenyl)silane dimethyl(2-ethylazapentalene)(2-methyl-4-phenylindenyl)silane dimethyl(2-ethylazapentalene)(2-methyl-4,5-benzoindenyl)silane dimethyl(2-ethylazapentalene)(2-ethyl-4-(4'-tert-butylphenyl-indenyl)silane dimethyl(2-ethylazapentalene)(2-methyl-4-(4'-tert-butylphenyl)indenyl)silane dimethyl(2-ethylazapentalene)(2-n-propyl-4-(4'-tert-butylphenyl)indenyl)silane dimethyl(2-methylthiapentalene)(2-methylindenyl)silane dimethyl(2-methylthiapentalene)(2-methyl-4-phenylindenyl)silane dimethyl(2-methylthiapentalene)(2-methyl-4,5-benzoindenyl)silane dimethyl(2-methylthiapentalene)(2-ethyl-4-(4'-tert-butylphenyl)indenyl)silane dimethyl(2-methylthiapentalene)(2-n-propyl-4-(4'-tert-butyl-phenyl)indenyl)silane dimethyl(2-ethylthiapentalene)(2-methylindenyl)silane dimethyl(2-ethylthiapentalene)(2-methyl-4-phenylindenyl)silane dimethyl(2-ethylthiapentalene)(2-methyl-4,5-benzoindenyl)silane dimethyl(2-ethylthiapentalene)(2-ethyl-4-(4'-tert-butylphenyl)indenyl)silane dimethyl(2-ethylthiapentalene)(2-n-propyl-4-(4'-tert-butylphenyl)indenyl)silane.

The bridged bisindenyl ligands of the formula (Va) can be used as starting materials in the process of the present invention either after isolation or as crude products in the form in which they are obtained in their synthesis without prior isolation. Such a single-vessel process for preparing metallocene dichlorides is described in DE 44 34 640.

In the process of the present invention, the metallocenes of the formula (IV) are prepared by reacting the ligand starting compounds of the formula (V) with transition metal compounds of the formula (Ia) in an inert solvent or solvent mixture in which the deprotonation of the substituted cyclopentadiene derivatives can also be carried out.

Suitable inert solvents are aliphatic or aromatic hydrocarbons, for example benzene, toluene, xylene, mesitylene, ethylbenzene, chlorobenzene, dichlorobenzene, fluorobenzene, decalin, tetralin, pentane, hexane, cyclohexane, heptane, 1,2-dichloroethane, dichloromethane, ethers such as diethyl ether, di-n-butyl ether, tert-butyl methyl ether (MTBE), tetrahydrofuran (THF), 1,2-dimethoxyethane (DME), anisole, triglyme, dioxane and any mixtures of these. Preference is given to solvents or solvent mixtures in which the metallization of the ligand starting compound of the formula (Va) and the subsequent reaction to form the metallocene complex of the formula (IV) can be carried out. Nonlimiting examples of such solvents/solvent mixtures are toluene, hexane, heptane, xylene, tetrahydrofuran (THF), dimethoxyethane (DME), toluene/THF, heptane/DME and toluene/DME.

The reaction of the ligand starting compounds of the formula (V) with the transition metal compounds of the formula (Ia) for preparing the metallocenes of the formula (IV) by the process of the present invention is generally carried out at from −78 to 150° C., preferably from 0 to 110° C., particularly preferably from 20 to 60° C.

The molar ratio of the transition metal compounds of the formula (Ia) to the ligand precursors of the formula (V) in the process of the present invention is generally in the range from 10 to 0.1, preferably from 2 to 0.5.

The concentration of ligand precursors of the formula (V) in the reaction mixture is generally from 0.0001 mol/l to 8 mol/l, preferably from 0.01 mol/l to 3 mol/l, particularly preferably from 0.1 mol/l to 2 mol/l.

The reaction time is generally in the range from 5 minutes to 1 week, preferably from 15 minutes to 24 hours.

The metallocenes of the formulae (II) and (IV) formed in the process of the present invention display a significantly better solubility in inert organic solvents than do the corresponding metallocene chlorides. For the purposes of the present invention, a significantly better solubility means that the molar concentrations in the organic solvent are at least doubled, preferably increased by a factor of more than four and very particularly preferably increased by a factor of more than eight.

Illustrative but nonlimiting examples of metallocenes of the formula (IV) obtainable by the stereoselective process of the present invention are:

dimethylsilanediylbis(2-methylindenyl)zirconium monochloride mono(2,6-dimethylphenoxide)

dimethylsilanediylbis(2-methyl-4-(1-naphthyl)indenyl) zirconium monochloride mono(2,6-dimethylphenoxide)

dimethylsilanediylbis(2-methyl-4-phenylindenyl) zirconium monochloride mono(2,6-dimethylphenoxide)

dimethylsilanediylbis(2-ethylindenyl)zirconium monochloride mono(2,6-dimethylphenoxide)

dimethylsilanediylbis(2-ethyl-4-phenylindenyl) zirconium monochloride mono(2,6-dimethylphenoxide)

dimethylsilanediylbis(2-methyl-4,5-benzoindenyl) zirconium monochloride mono(2,6-dimethylphenoxide)

dimethylsilanediylbis (2-methyl-4,6 diisopropylindenyl) zirconium monochloride mono(2,6-dimethylphenoxide)

dimethylsilanediylbis(2,4,6-trimethylindenyl)zirconium monochloride mono(2,6-dimethylphenoxide)

dimethylsilanediylbis(2,5,6-trimethylindenyl)zirconium monochloride mono(2,6-dimethylphenoxide)

dimethylsilanediylbis(2,4,7-trimethylindenyl)zirconium monochloride mono(2,6-dimethylphenoxide)

dimethylsilanediylbis(2-methyl-5-isobutylindenyl) zirconium monochloride mono(2,6-dimethylphenoxide)

dimethylsilanediylbis(2-methyl-5-t-butylindenyl) zirconium monochloride mono(2,6-dimethylphenoxide)

1,2-ethanediylbis(2-methyl-4-phenylindenyl)zirconium monochloride mono(2,6-dimethylphenoxide)

1,2-ethanediylbis(2-methyl-4,5-benzoindenyl)zirconium monochloride mono(2,6-dimethylphenoxide)

1,2-ethanediylbis(2,4,7-trimethylindenyl)zirconium monochloride mono(2,6-dimethylphenoxide)

1,2-ethanediylbis(2-methylindenyl)zirconium monochloride mono(2,6-dimethylphenoxide)

dimethylsilanediylbis(2-methyl-4-(4'-tert-butylphenyl) indenyl)zirconium monochloride mono(2,6-dimethylphenoxide)

dimethylsilanediylbis(2-methyl-4-(3',5'-di-tert-butylphenyl)indenyl)zirconium monochloride mono(2,6-dimethylphenoxide)

methylidenebis(2-methyl-4-(4'-tert-butylphenyl)indenyl)zirconium monochloride mono(2,6-dimethylphenoxide)

isopropylidenebis(2-methyl-4-(4'-tert-butylphenyl)indenyl)zirconium monochloride mono(2,6-dimethylphenoxide)

dimethylsilanediylbis(2-methyl-4-(4'-methylphenyl)indenyl)zirconium monochloride mono(2,6-dimethylphenoxide)

dimethylsilanediylbis(2-ethyl-4-phenyl)indenyl)zirconium monochloride mono(2,6-dimethylphenoxide)

dimethylsilanediylbis(2-ethyl-4-(4'-methylphenyl)indenyl)zirconium monochloride mono(2,6-dimethylphenoxide)

dimethylsilanediylbis(2-ethyl-4-(4'-tert-butylphenyl)indenyl)zirconium monochloride mono(2,6-dimethylphenoxide)

dimethylsilanediylbis(2-ethyl-4-(3'5'-di-tert-butylphenyl)indenyl)zirconium monochloride mono(2,6-dimethylphenoxide)

methylidenebis(2-ethyl-4-(4'-tert-butylphenyl)indenyl)zirconium monochloride mono(2,6-dimethylphenoxide)

isopropylidenebis(2-ethyl-4-(4'-tert.-butylphenyl)indenyl)zirconium monochloride mono(2,6-dimethylphenoxide)

dimethylsilanediylbis(2-n-propyl-4-phenyl)indenyl)zirconium monochloride mono(2,6-dimethylphenoxide)

dimethylsilanediylbis(2-n-propyl-4-(4'-methylphenyl)indenyl)zirconium monochloride mono(2,6-dimethylphenoxide)

dimethylsilanediylbis(2-n-propyl-4-(4'-tert-butylphenyl)indenyl)zirconium monochloride mono(2,6-dimethylphenoxide)

dimethylsilanediylbis(2-n-propyl-4-(3'5'-di-tert-butylphenyl)indenyl)zirconium monochloride mono(2,6-dimethylphenoxide)

methylidenebis(2-n-propyl-4-(4'-tert-butylphenyl)indenyl)zirconium monochloride mono(2,6-dimethylphenoxide)

isopropylidenebis(2-n-propyl-4-(4'-tert-butylphenyl)indenyl)zirconium monochloride mono(2,6-dimethylphenoxide)

dimethylsilanediylbis(2-isopropyl-4-phenyl)indenyl)zirconium monochloride mono(2,6-dimethylphenoxide)

dimethylsilanediylbis(2-isopropyl-4-(4'-methylphenyl)indenyl)zirconium monochloride mono(2,6-dimethylphenoxide)

dimethylsilanediylbis(2-isopropyl-4-(4'-tert-butylphenyl)indenyl)zirconium monochloride mono(2,6-dimethylphenoxide)

methylidenebis(2-isopropyl-4-(4'-tert-butylphenyl)indenyl)zirconium monochloride mono(2,6-dimethylphenoxide)

isopropylidenebis(2-isopropyl-4-(4'-tert-butylphenyl)indenyl)zirconium monochloride mono(2,6-dimethylphenoxide)

dimethylsilanediylbis(2-n-butyl-4-phenyl)indenyl)zirconium monochloride mono(2,6-dimethylphenoxide)

dimethylsilanediylbis(2-n-butyl-4-(4'-methylphenyl)indenyl)zirconium monochloride mono(2,6-dimethylphenoxide)

dimethylsilanediylbis(2-n-butyl-4-(4'-tert-butylphenyl)indenyl)zirconium monochloride mono(2,6-dimethylphenoxide)

dimethylsilanediylbis(2-(2-methylpropyl)-4-phenyl)indenyl)zirconium monochloride mono(2,6-dimethylphenoxide)

dimethylsilanediylbis(2-(2-methylpropyl)-4-(4'-methylphenyl)indenyl)zirconium monochloride mono(2,6-dimethylphenoxide)

dimethylsilanediylbis(2-(2-methylpropyl)-4-(4'-tert-butylphenyl)indenyl)zirconium monochloride mono(2,6-dimethylphenoxide)

1,2-ethanediylbis(2-methyl-4-(4'-tert-butylphenyl)indenyl)zirconium monochloride mono(2,6-dimethylphenoxide)

1,2-ethanediylbis(2-ethyl-4-phenyl)indenyl)zirconium monochloride mono(2,6-dimethylphenoxide)

1,2-ethanediylbis(2-ethyl-4-(4'-tert-butylphenyl)indenyl)zirconium monochloride mono(2,6-dimethylphenoxide)

1,2-ethanediylbis(2-n-propyl-4-phenyl)indenyl)zirconium monochloride mono(2,6-dimethylphenoxide)

1,2-ethanediylbis(2-n-propyl-4-(4'-tert-butylphenyl)indenyl)zirconium monochloride mono(2,6-dimethylphenoxide)

1,2-ethanediylbis (2-isopropyl-4-(4-phenyl) indenyl) zirconium monochloride mono(2,6-dimethylphenoxide)

1,2-ethanediylbis(2-isopropyl-4-(4'-tert-butylphenyl)indenyl)zirconium monochloride mono(2,6-dimethylphenoxide)

1,2-ethanediylbis(2-(2-methylpropyl)-4-(4-phenyl)indenyl)zirconium monochloride mono(2,6-dimethylphenoxide)

1,2-ethanediylbis(2-(2-methylpropyl)-4-(4'-tert-butylphenyl)indenyl)zirconium monochloride mono(2,6-dimethylphenoxide)

Further examples of compounds of the formula (VI) obtainable in the stereoselective process of the present invention are metallocenes of the abovementioned type in which the zirconium fragment "zirconium monochloride mono(2,6-dimethylphenoxide)" is replaced by zirconium monochloride mono(2,4-di-tert-butylphenoxide), zirconium monochloride mono(2-methylphenoxide), zirconium monochloride mono(2-isopropylphenoxide), zirconium monochloride mono(2,4-dimethylphenoxide), zirconium monochloride mono(2,3-dimethylphenoxide), zirconium monochloride mono(2,4,6-trimethylphenoxide), zirconium monochloride mono(2-isopropyl-5-methylphenoxide), zirconium monochloride mono(2-tert-butyl-6-methylphenoxide), zirconium monochloride mono(2,6-di-isopropylphenoxide), zirconium monochloride mono (2,6-di-tert-butylphenoxide), zirconium monochloride mono(1-naphthoxide) and zirconium monochloride mono(2-phenylphenoxide).

The process of the present invention can be employed for stereoselectively preparing easily purifiable metallocene catalyst components, in particular of the formula (IV), which can be used in the same manner as the difficult-to-purify 1:1 mixtures of rac/meso-ansa-bisindenylzirconium dichlorides as catalyst components in the polymerization of propylene.

The metallocenes of the formulae (II) and (IV) obtainable in the process of the present invention are particularly suitable as constituents of catalyst systems for preparing polyolefins by polymerization of at least one olefin in the presence of a catalyst comprising at least one cocatalyst and at least one metallocene. For the purposes of the present invention, the term polymerization refers to both homopolymerization and copolymerization.

The metallocenes of the formulae (II) and (IV), in particular of the formula (IV), obtainable in the process of the present invention can be used for the polymerization of one or more olefins of the formula $R^\alpha$—CH=CH—$R^\beta$, where $R^\alpha$ and $R^\beta$ are identical or different and are each a hydrogen atom or a hydrocarbon having from 1 to 20 carbon atoms, in particular from 1 to 10 carbon atoms, and $R^\alpha$ and $R^\beta$ together with the atoms connecting them may form one or more rings. Examples of such olefins are 1-olefins having 2–40 carbon atoms, preferably from 2 to 10 carbon atoms, e.g. ethene, propene, 1-butene, 1-pentene, 1-hexene, 4-methyl-1-pentene or 1-octene, styrene, dienes such as 1,3-butadiene, 1,4-hexadiene, vinylnorbornene, norbornadiene, ethylnorbornadiene and cyclic olefins such as norbornene, tetracyclododecene or methylnorbornene. Preference is given to homopolymerizing ethylene or propylene, or copolymerizing ethylene with one or more cyclic olefins such as norbornene and/or one or more dienes having from 4 to 20 carbon atoms, e.g. 1,3-butadiene or 1,4-hexadiene. Examples of such copolymers are ethylene/norbornene copolymers, ethylene/propylene copolymers and ethylene/propylene/1,4-hexadiene copolymers.

The metallocenes of the formulae (II) and (IV) obtained in the process of the present invention display activities in the polymerization of olefins which are at least equal to and sometimes higher than those of the dihalide compounds, and the polyolefins obtained display a reduction in the undesirable low molecular weight extractable components.

The polymerization is carried out at from −60 to 300° C., preferably from 50 to 200° C., very particularly preferably 50–80° C. The pressure is from 0.5 to 2000 bar, preferably from 5 to 64 bar.

The polymerization can be carried out in solution, in bulk, in suspension or in the gas phase, continuously or batchwise, in one or more stages. Preferred embodiments are gas-phase polymerization and bulk polymerization.

The catalyst used preferably comprises one of the metallocene compounds obtainable in the process of the present invention. It is also possible to use mixtures of two or more metallocene compounds, e.g. for preparing polyolefins having a broad or multimodal molar mass distribution.

The cocatalyst, which together with one of the metallocenes of the formulae (II) and (IV) obtainable by the process of the present invention forms the catalyst system, comprises at least one compound such as an aluminoxane or a Lewis acid or an ionic compound which reacts with a metallocene to convert it into a cationic compound.

As aluminoxane, preference is given to using a compound of the formula (VII)

$$(RAlO)_n \qquad (VII)$$

Further suitable aluminoxanes may be, for example, cyclic as in formula (VIII)

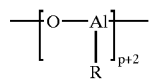

or linear as in formula (IX)

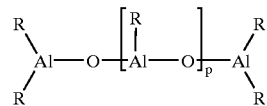

or of the cluster type as in formula (X)

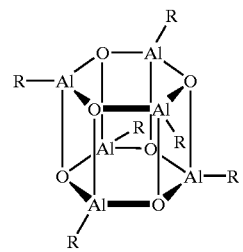

Such aluminoxanes are described, for example, in JACS 117 (1995), 6465–74, Organometallics 13 (1994), 2957–2969.

The radicals R in the formulae (VII), (VIII), (IX) and (X) may be identical or different and can be a $C_1$–$C_{20}$-hydrocarbon group such as a $C_1$–$C_6$-alkyl group, a $C_6$–$C_{18}$-aryl group, benzyl or hydrogen, and p is an integer from 2 to 50, preferably from 10 to 35.

The radicals R are preferably identical and are methyl, isobutyl, n-butyl, phenyl or benzyl, particularly preferably methyl.

If the radicals R are different, they are preferably methyl and hydrogen, methyl and isobutyl or methyl and n-butyl, with hydrogen or isobutyl or n-butyl preferably being present in an amount of 0.01–40% (number of radicals R).

The aluminoxane can be prepared in various ways by known methods. One of the methods is, for example, to react an aluminum-hydrocarbon compound and/or a hydridoaluminum-hydrocarbon compound with water (gaseous, solid, liquid or bound—for example as water of crystallization) in an inert solvent (e.g. toluene).

To prepare an aluminoxane having different alkyl groups R, two different trialkylaluminums ($AlR_3$+$AlR'_3$) corresponding to the desired composition and reactivity are reacted with water (cf. S. Pasynkiewicz, Polyhedron 9 (1990) 429 and EP-A-0,302,424).

Regardless of the method of preparation, all aluminoxane solutions have a variable content of unreacted aluminum starting compound which is present in free form or as adduct.

As Lewis acid, preference is given to using at least one organoboron or organoaluminum compound containing $C_1$–$C_{20}$ groups such as branched or unbranched alkyl or haloalkyl, e.g. methyl, propyl, isopropyl, isobutyl, trifluoromethyl, unsaturated groups such as aryl or haloaryl, e.g. phenyl, tolyl, benzyl, p-fluorophenyl, 3,5-difluorophenyl, pentachlorophenyl, pentafluorophenyl, 3,4,5-trifluorophenyl and 3,5-di(trifluoromethyl)phenyl.

Examples of Lewis acids are trimethylaluminum, triethylaluminum, triisobutylaluminum, tributylaluminum, trifluoroborane, triphenylborane, tris(4-fluorophenyl)borane, tris(3,5-difluorophenyl) borane, tris(4-fluoromethylphenyl)borane, tris(pentafluorophenyl)borane, tris(tolyl)borane, tris(3,5-dimethylphenyl)borane, tris(3,5-difluorophenyl)borane, [(C$_6$F$_5$)$_2$BO]$_2$Al—Me, [(C$_6$F$_5$)$_2$BO]$_3$Al and/or tris(3,4,5-trifluorophenyl)borane. Particular preference is given to tris(pentafluorophenyl)borane.

As ionic cocatalysts, preference is given to using compounds which contain a noncoordinating anion, for example tetrakis(pentafluorophenyl)borates, tetraphenylborates, SbF$_6$—, CF$_3$SO$_3$— or ClO$_4$—. Cationic counterions used are protonated Lewis bases such as methylamine, aniline, dimethylamine, diethylamine, N-methylaniline, diphenylamine, N,N-dimethylaniline, trimethylamine, triethylamine, tri-n-butylamine, methyldiphenylamine, pyridine, p-bromo-N,N-dimethylaniline, p-nitro-N,N-dimethylaniline, triethylphosphine, triphenylphosphine, diphenylphosphine, tetrahydrothiophene or triphenylcarbenium.

Examples of such ionic compounds are:
triethylammonium tetra(phenyl)borate,
tributylammonium tetra(phenyl)borate,
trimethylammonium tetra(tolyl)borate,
tributylammonium tetra(tolyl)borate,
tributylammonium tetra(pentafluorophenyl)borate,
tributylammonium tetra(pentafluorophenyl)aluminate,
tripropylammonium tetra(dimethylphenyl)borate,
tributylammonium tetra(trifluoromethylphenyl)borate,
tributylammonium tetra(4-fluorophenyl)borate,
N,N-dimethylanilinium tetra(phenyl)borate,
N,N-diethylanilinium tetra(phenyl)borate,
N,N-dimethylanilinium tetrakis(pentafluorophenyl)borate,
N,N-dimethylanilinium tetrakis(pentafluorophenyl)aluminate,
di(propyl)ammonium tetrakis(pentafluorophenyl)borate,
di(cyclohexyl)ammonium tetrakis(pentafluorophenyl)borate,
triphenylphosphonium tetrakis(phenyl)borate,
triethylphosphonium tetrakis(phenyl)borate,
diphenylphosphonium tetrakis(phenyl)borate,
tri(methylphenyl)phosphonium tetrakis(phenyl)borate,
tri(dimethylphenyl)phosphonium tetrakis(phenyl)borate,
triphenylcarbenium tetrakis(pentafluorophenyl)borate,
triphenylcarbenium tetrakis(pentafluorophenyl)aluminate,
triphenylcarbenium tetrakis(phenyl)aluminate,
ferrocenium tetrakis(pentafluorophenyl)borate and/or
ferrocenium tetrakis(pentafluorophenyl)aluminate.

Preference is given to triphenylcarbenium tetrakis(pentafluorophenyl)borate and/or
N,N-dimethylanilinium tetrakis(pentafluorophenyl)borate.

It is also possible to use mixtures of at least one Lewis acid and at least one ionic compound.

Further compounds suitable as cocatalyst components are borane or carborane compounds such as
7,8-dicarbaundecaborane(13),
undecahydrido-7,8-dimethyl-7,8-dicarbaundecaborane,
dodecahydrido-1-phenyl-1,3-dicarbanonaborane,
tri(butyl)ammonium undecahydrido-8-ethyl-7,9-dicarbaundecaborate,
4-carbanonaborane(14),
bis(tri(butyl)ammonium) nonaborate,
bis(tri(butyl)ammonium) undecaborate,
bis(tri(butyl)ammonium) dodecaborate,
bis(tri(butyl)ammonium) decachlorodecaborate,
tri(butyl)ammonium 1-carbadecaborate,
tri(butyl)ammonium 1-carbadodecaborate,
tri(butyl)ammonium 1-trimethylsilyl-1-carbadecaborate,
tri(butyl)ammonium bis(nonahydrido-1,3-dicarbanonaborato)cobaltate(III),
tri(butyl)ammonium bis(undecahydrido-7,8-dicarbaundecaborato)ferrate(III).

Further cocatalysts which can be used, either in unsupported or supported form, are the compounds mentioned in EP-A-0924223, DE-A-19622207, EP-A-0601830, EP-A-0824112, EP-A-0824113, WO 99/06414, EP-A-0811627 and DE-A-19804970.

The support component of the catalyst system can be any organic or inorganic, inert solid, in particular a porous support such as talc, inorganic oxides and finely divided polymer powders (e.g. polyolefins).

Suitable inorganic oxides may be found among those of elements of groups 2, 3, 4, 5, 13, 14, 15 and 16 of the Periodic Table of the Elements. Examples of oxides preferred as supports include silicon dioxide, aluminum oxide, and also mixed oxides of the two elements and corresponding oxide mixtures. Other inorganic oxides which may be used alone or in combination with the lastmentioned preferred oxidic supports are, for example, MgO, ZrO$_2$, TiO$_2$ or B$_2$O$_3$, to name only a few.

The support materials used have a specific surface area in the range from 10 to 1000 m$^2$/g, a pore volume in the range from 0.1 to 5 ml/g and a mean particle size of from 1 to 500 μm. Preference is given to supports having a specific surface area in the range from 50 to 500 m$^2$/g, a pore volume in the range from 0.5 to 3.5 ml/g and a mean particle size in the range from 5 to 350 μm. Particular preference is given to supports having a specific surface area in the range from 200 to 400 m$^2$/g, a pore volume in the range from 0.8 to 3.0 ml/g and a mean particle size of from 10 to 200 μm.

If the support material used naturally has a low moisture content or residual solvent content, dehydration or drying before use can be omitted. If this is not the case, as when using silica gel as support material, dehydration or drying is advisable. Thermal dehydration or drying of the support material can be carried out under reduced pressure and with simultaneous inert gas blanketing (e.g. nitrogen). The drying temperature is in the range from 100 to 1000° C., preferably from 200 to 800° C. In this case, the pressure is not critical. The duration of the drying process can be from 1 to 24 hours. Shorter or longer drying times are possible, provided that equilibrium with the hydroxyl groups on the support surface can be established under the conditions chosen, which normally takes from 4 to 8 hours.

Dehydration or drying of the support material can also be carried out by chemical means, by reacting the absorbed water and the hydroxyl groups on the surface with suitable passivating agents. The reaction with the passivating reagent can convert all or some of the hydroxyl groups into a form which leads to no adverse interaction with the catalytically active centers. Suitable passivating agents are, for example, silicon halides and silanes, e.g. silicon tetrachloride, chlorotrimethylsilane, dimethylaminotrichlorosilane, or organometallic compounds of aluminum, boron and magnesium, for example trimethylaluminum, triethylaluminum, triisobutylaluminum, triethylborane, dibutylmagnesium. Chemical dehydration or passivation of the support material is carried out, for example, by reacting a suspension of the support material in a suitable solvent with the passivating reagent in pure form or as a solution in a suitable solvent in the absence of air and moisture. Suitable solvents are, for example, aliphatic or aromatic hydrocarbons such as pentane, hexane, heptane, toluene or xylene. Passivation is carried out at from 25° C. to 120° C., preferably from 50 to 70° C. Higher and lower temperatures are possible. The reaction time is from 30 minutes to 20 hours, preferably from 1 to 5 hours. After chemical dehydration is complete, the support material is isolated by filtration under inert conditions, washed one or more times with suitable inert solvents as described above and subsequently dried in a stream of inert gas or under reduced pressure.

Organic support materials such as finely divided polyolefin powders (e.g. polyethylene, polypropylene or polystyrene) can also be used and should likewise be freed of adhering moisture, solvent residues or other impurities by appropriate purification and drying operations before use.

The catalyst system is prepared by mixing at least one metallocene, at least one cocatalyst and at least one passivated support.

To prepare the supported catalyst system, at least one of the above-described metallocene components obtainable by the process of the present invention is brought into contact with at least one cocatalyst component in a suitable solvent, preferably giving a soluble reaction product, an adduct or a mixture. The composition obtained in this way is then mixed with the dehydrated or passivated support material, the solvent is removed and the resulting supported metallocene catalyst system is dried to ensure that all or most of the solvent is removed from the pores of the support material. The supported catalyst is obtained as a free-flowing powder.

A method of preparing a free-flowing and, if desired, prepolymerized supported catalyst system comprises the following steps:

a) preparation of a metallocene/cocatalyst mixture in a suitable solvent or suspension medium, where the metallocene component is obtainable from the process of the present invention and has the structures described above, b) application of the metallocene/cocatalyst mixture to a porous, preferably inorganic dehydrated support, c) removal of the major part of the solvent from the resulting mixture, d) isolation of the supported catalyst system, e) if desired, prepolymerization of the resulting supported catalyst system with one or more olefinic monomer(s) to give a prepolymerized supported catalyst system.

Preferred solvents for the preparation of the metallocene/cocatalyst mixture are hydrocarbons and hydrocarbon mixtures which are liquid at the chosen reaction temperature and in which the individual components preferably dissolve. However, solubility of the individual components is not a prerequisite as long as it is ensured that the reaction product of metallocene and cocatalyst components is soluble in the solvent chosen. Examples of suitable solvents include alkanes such as pentane, isopentane, hexane, heptane, octane and nonane; cycloalkanes such as cyclopentane and cyclohexane; and aromatics such as benzene, toluene, ethylbenzene and diethylbenzene. Very particular preference is given to toluene.

The amounts of aluminoxane and metallocene used in the preparation of the supported catalyst system can be varied over a wide range. Preference is given to a molar ratio of aluminum to transition metal in the metallocene of from 10:1 to 1000:1, very particularly preferably from 50:1 to 500:1.

In the case of methylaluminoxane, preference is given to using 30% strength solutions in toluene; however, the use of 10% strength solutions is also possible.

For preactivation, the metallocene in the form of a solid is dissolved in a solution of the aluminoxane in a suitable solvent. However, it is also possible to dissolve the metallocene separately in a suitable solvent and subsequently to combine this solution with the aluminoxane solution. Preference is given to using toluene.

The preactivation time is from 1 minute to 200 hours. Preactivation can take place at room temperature (25° C.). In some cases, the use of higher temperatures can shorten the preactivation time required and effect an additional increase in activity. In this case, "higher temperatures" means a range from 50 to 100° C.

The preactivated solution or the metallocene/cocatalyst mixture is subsequently combined with an inert support material, usually silica gel, which is in the form of a dry powder or in the form of a suspension in one of the abovementioned solvents. The support material is preferably used as a powder. The order of addition is immaterial. The preactivated metallocene/cocatalyst solution or the metallocene/cocatalyst mixture can be added to the support material or else the support material can be introduced into the solution.

The volume of the preactivated solution or of the metallocene/cocatalyst mixture can exceed 100% of the total pore volume of the support material used or else can be up to 100% of the total pore volume.

The temperature at which the preactivated solution or the metallocene/cocatalyst mixture is brought into contact with the support material can vary from 0 to 100° C. Lower or higher temperatures are, however, also possible.

Subsequently, the solvent is completely or mostly removed from the supported catalyst system, with the mixture being able to be stirred and, if desired, also heated. Preference is given to removing both the visible proportion of the solvent and the proportion present in the pores of the support material. The removal of the solvent can be carried out in a conventional way using reduced pressure and/or flushing with inert gas. In the drying process, the mixture can be heated until the free solvent has been removed, which usually takes from 1 to 3 hours at a preferred temperature of from 30 to 60° C. The free solvent is the visible proportion of solvent in the mixture. For the purposes of the present invention, residual solvent is the proportion enclosed in the pores.

As an alternative to complete removal of the solvent, it is also possible to dry the supported catalyst system only to a certain residual solvent content, with the free solvent having been completely removed. The supported catalyst system can subsequently be washed with a low-boiling hydrocarbon such as pentane or hexane and dried again.

The supported catalyst system prepared can either be used directly for the polymerization of olefins or can be prepolymerized using one or more olefinic monomers before use in a polymerization process. The prepolymerization of supported catalyst systems is described, for example, in WO 94/28034.

As additive, it is possible to add a small amount of an olefin, preferably an α-olefin (for example styrene or phenyldimethylvinylsilane) as activity-promoting component or, for example, an antistatic.

As antistatic, use is usually made of a mixture of a metal salt of Medialan acid, a metal salt of anthranilic acid and a polyamine. Such antistatics are described, for example, in EP-A-0,636,636.

The molar ratio of additive to metallocene component (compound (I)) is preferably from 1:1000 to 1000:1, very particularly preferably from 1:20 to 20:1.

The present invention also provides a process for preparing a polyolefin by polymerization of one or more olefins in the presence of the catalyst system comprising at least one transition metal component of the formula (II) or (IV) obtainable by the process of the present invention. For the purposes of the present invention, polymerization encompasses both homopolymerization and copolymerization.

The metallocenes of the formulae (II) and (IV) obtained in the process of the present invention display activities in the polymerization of olefins which are at least equal to and sometimes greater than those of the dihalide compounds, and the polyolefins obtained display a reduction in the amount of undesirable low molecular weight extractable components.

The catalyst system prepared can be used as sole catalyst component for the polymerization of olefins having from 2 to 20 carbon atoms, or preferably in combination with at least one alkyl compound of the Elements of main groups I to III of the Periodic Table, e.g. an aluminum, magnesium or lithium alkyl or an aluminoxane. The alkyl compound is added to the monomers or the suspension medium and serves to free the monomers of substances which could adversely affect the catalyst activity. The amount of alkyl compound added depends on the quality of the monomers used.

As molar mass regulator and/or to increase the activity, hydrogen is added if required.

In the polymerization, the antistatic can be introduced into the polymerization system together with or separately from the catalyst system used.

The polymers prepared using the catalyst system comprising at least one of the metallocenes of the formulae (II) and (IV) obtained in the process of the present invention display uniform particle morphology and contain no fines. No deposits or cake material are obtained in the polymerization using the catalyst system.

The catalyst system gives polymers such as polypropylene having an extraordinarily high stereospecificity and regiospecificity.

The stereospecificity and regiospecificity of polymers, in particular polypropylene, is characterized in particular by the triad tacticity (TT) and the proportion of 2-1-inserted propene units (RI), which can be determined from the $^{13}$C-NMR spectra.

The $^{13}$C-NMR spectra are measured in a mixture of hexachlorobutadiene and $d_2$-tetrachloroethane at elevated temperature (365 K). All $^{13}$C-NMR spectra of the polypropylene samples measured are calibrated on the basis of the resonance signal of $d_2$-tetrachloroethane ($\delta$=73.81 ppm).

To determine the triad tacticity of polypropylene, the methyl resonance signals in the range from 23 to 16 ppm in the $^{13}$C-NMR spectrum are examined; cf. J. C. Randall, Polymer Sequence Determination: Carbon-13 NMR Method, Academic Press New York 1978; A. Zambelli, P. Locatelli, G. Bajo, F. A. Bovey, Macromolecules 8 (1975), 687–689; H. N. Cheng, J. A. Ewen, Makromol. Chem. 190 (1989), 1931–1943. Three successive 1–2-inserted propene units whose methyl groups are located on the same side in the "Fischer projection" are referred to as mm triads ($\delta$=21.0 ppm to 22.0 ppm). If only the second methyl group of the three successive propene units points to the other side, this sequence is referred to as an rr triad ($\delta$=19.5 ppm to 20.3 ppm) and if only the third methyl group of the three successive propene units points to the other side, as an mr triad ($\delta$=20.3 ppm to 21.0 ppm). The triad tacticity is calculated according to the following formula:

$$TT(\%)=mm/(mm+mr+rr)\cdot 100$$

If a propene unit is inserted inversely into the growing polymer chain, this is referred to as a 2-1-insertion; cf. T. Tsutsui, N. Ishimaru, A. Mizuno, A. Toyota, N. Kashiwa, Polymer 30, (1989), 1350–56. The following different structural arrangements are possible:

$$-CH_2-\underset{\underset{CH_3}{|}}{CH}-\overset{\alpha,\alpha}{CH_2}-\underset{\underset{CH_3}{|}}{CH}-\underset{\underset{CH_3}{|}}{CH}-\overset{\alpha,\beta}{CH_2}-\overset{\alpha,\beta}{CH_2}-\underset{\underset{CH_3}{|}}{CH}-CH_2-\underset{\underset{CH_3}{|}}{CH}-$$

$$-CH_2-\underset{\underset{CH_3}{|}}{CH}-\overset{\alpha,\alpha}{CH_2}-\underset{\underset{CH_3}{|}}{CH}-\underset{\underset{CH_3}{|}}{CH}-\overset{\alpha,\beta}{CH_2}-\overset{\alpha,\beta}{CH_2}-\underset{\underset{CH_3}{|}}{CH}-CH_2-\underset{\underset{CH_3}{|}}{CH}-$$

$$-CH_2-\underset{\underset{CH_3}{|}}{CH}-CH_2-CH_2-\overset{\alpha,\delta}{CH_2}-CH_2-\underset{\underset{CH_3}{|}}{CH}-CH_2-\underset{\underset{CH_3}{|}}{CH}-CH_2-$$

The proportion of 2-1-inserted propene units (RI) can be calculated according to the following formula:

$$RI(\%)=0.5\ I\alpha,\beta(I\alpha,\alpha+I\alpha,\beta+I\alpha,\delta)\cdot 100,$$

where $I\alpha,\alpha$ is the sum of the intensities of the resonance signals at $\delta$=41.84, 42.92 and 46.22 ppm, $I\alpha,\beta$ is the sum of the intensities of the resonance signals at $\delta$=30.13, 32.12, 35.11 and 35.57 ppm and $I\alpha,\delta$ is the intensity of the resonance signal at $\delta$=37.08 ppm.

The isotactic polypropylene which has been prepared using the catalyst system has a proportion of 2-1-inserted propene units RI of <0.5% at a triad tacticity TT of >98.0% and a melting point of >153° C., and the $M_w/M_n$ of the polypropylene prepared according to the present invention is from 2.5 to 3.5.

The copolymers which can be prepared using the catalyst system have a significantly higher molar mass than those of the prior art. At the same time, such copolymers can be prepared at high productivity at industrially relevant process parameters without deposition formation when using the catalyst system.

The polymers prepared by the process of the present invention are particularly suitable for producing hard and stiff shaped bodies having a high tensile strength, e.g. fibers, filaments, injection-molded parts, films, sheets or large hollow bodies (e.g. pipes).

The invention is illustrated by the following nonlimiting examples.

General information: Preparation and handling of organometallic compounds was carried out with exclusion of air and moisture under argon (Schlenk technique or glove box). All solvents required were purged with argon and dried over molecular sieves before use.

EXAMPLE 1

Preparation of Zirconium Monochloride Mono(O-2, 6-Me$_2$C$_6$H$_3$) (THF)$_2$ (1)

The preparation of (1) was carried out using a method analogous to that of H. Yasuda et al., J. Organomet. Chem.

493 (1994), page 113. Reaction of 4.4 g (19 mmol) of zirconium tetrachloride with 3.8 g (19.7 mmol) of $Me_3SiO$-2,6-$Me_2C_6H_3$ and crystallization gave 5.3 g (61%) of (1).

EXAMPLE 2

Preparation of Zirconium Monochloride Mono(O-2,4-(tert-Bu)$_2C_6H_3$) (THF)$_2$ (2)

The preparation of (2) was carried out using a method analogous to Example 1. Reaction of 6.9 g (30 mmol) of zirconium tetrachloride and 8.4 g (30 mmol) of $Me_3SiO$-2,4-(tert-Bu)$_2C_6H_3$ and crystallization gave 9.0 g (55%) of (2).

1H-NMR (400 MHz, CDCl$_3$): 7.5 (1H), 7.3 (1H), 7.15 (dd, 1H), 4.5 (br., 8H), 2.1 (br., 8H), 1.5 (s, 9H), 1.3 (s, 9H).

EXAMPLE 3

Pseudo-rac-Dimethylsilanediylbis(2-methyl-4,5-benzo-indenyl)zirconium Monochloride Mono(2,4-di-tert-butylphenoxide) (3)

A solution of 4 g (9.6 mmol) of dimethylbis(2-methyl-4,5-benzoindenyl)silane in 38 ml of toluene/1.6 ml of THF was admixed with 7.2 ml (19.2 mmol) of a 20% strength solution of n-butyllithium in toluene and the mixture was stirred at 60° C. for 1 hour. 5.25 g (9.6 mmol) of (2) were added thereto at 20° C. and the reaction mixture was stirred at 30° C. for 1 hour. The $^1$H-NMR spectrum of a sample of the suspension showed a pseudo-rac/pseudo-meso ratio of 4:1. The reaction mixture was filtered through Celite, the filter cake was extracted with a total of 125 ml of hot toluene and the filtrate was evaporated to about 70 ml. After crystallization at −30° C., the yellow crystalline precipitate was isolated by filtration, washed with a little cold toluene and dried under reduced pressure. This gave 3.2 g (44%) of (3).

1H-NMR (400 MHz, CDCl$_3$): 8.05 (dd, 1H), 7.75 (m, 2H), 7.65 (dd, 1H), 7.60 (1H), 7.5–7.15 (m, 6H), 7.1 (m, 1H), 7.0 (m, 1H), 6.85 (s, 1H), 6.8 (d, 1H), 6.65 (m, 1H), 5.45 (d, 1H), 2.82 (s, 3H), 2.45 (s, 3H), 1.45 (s, 3H), 1.35 (s, 3H), 1.25 (s, 9H), 0.95 (s, 9H).

COMPARATIVE EXAMPLE

Rac-Dimethylsilanediylbis(2-methyl-4,5-benzoindenyl)zirconium Dichloride

A solution of 2.5 g (6.0 mmol) of dimethylbis(2-methyl-4,5-benzoindenyl)silane in 18 ml of toluene/2 ml of THF was admixed with 4.5 ml (12.0 mmol) of a 20% strength solution of n-butyllithium in toluene and the mixture was stirred at 50° C. for 2 hours. 2.26 g (6.0 mmol) of ZrCl$_4$*(THF)$_2$ were added thereto at 40° C., and the reaction mixture was stirred at 40° C. for ½ an hour. The $^1$H-NMR spectrum of a sample of the suspension showed an rac/meso ratio of 1:1. The reaction mixture was filtered, the yellow product was extracted with a total of 30 ml of methylene chloride and twice with 5 ml each time of THF. After drying under reduced pressure, 0.7 g (20%) of rac-dimethylsilanediylbis(2-methyl-4,5-benzoindenyl) zirconium dichloride was obtained.

Solubility Comparison:

50 mg of rac-dimethylsilanediylbis(2-methyl-4,5-benzoindenyl)zirconium dichloride dissolved completely in 240 ml of toluene at room temperature (solubility: about 0.36 mmol/l).

50 mg of the compound (3) dissolved immediately in <5 ml of toluene at room temperature (solubility: >13 mmol/l).

EXAMPLE 3a

Preparation of Catalyst Using (3) and Polymerization 35.1 mg (0.047 mmol) of (3) were stirred in 2.1 ml of 30% strength MAO solution in toluene (Al/Zr=215) for 60 minutes at room temperature. 2 g of SiO$_2$ (Grace XPO2107, pretreated at 140° C., 10 mbar, 10 hours) were subsequently added and the mixture was stirred for another 10 minutes. The solvent was removed in an oil pump vacuum.

A dry 2 l reactor was flushed firstly with nitrogen and subsequently propylene and charged with 1.5 l of liquid propylene. 2 ml of TEA (20% strength in Varsol) were added and the mixture was stirred for 15 minutes. The catalyst system prepared above (0.886 g) was then resuspended in 20 ml of heptane and injected into reactor and rinsed in using 15 ml of heptane. The reaction mixture was heated to the polymerization temperature of 60° C. and polymerization was carried out for one hour. The polymerization was stopped by venting the remaining propylene. The polymer was dried in a vacuum drying oven. This gave 470 g of polypropylene powder. The reactor displayed no deposits on the inner wall or stirrer. The catalyst activity was 0.53 kg of PP/g of catalyst x h.

COMPARATIVE EXAMPLE

Preparation of catalyst using dimethylsilanediylbis(2-methyl-4,5-benzoindenyl)zirconium dichloride and polymerization 27.1 mg (0.047 mmol) of dimethylsilanediylbis(2-methyl-4,5-benzoindenyl)zirconium dichloride were stirred in 2.1 ml of 30% strength MAO solution in toluene (Al/Zr=215) for 60 minutes at room temperature. 2 g of SiO$_2$ (Grace XPO2107, pretreated at 140° C., 10 mbar, 10 hours) were subsequently added and the mixture was stirred for another 10 minutes. The solvent was removed in an oil pump vacuum.

A dry 2 l reactor was flushed firstly with nitrogen and subsequently propylene and charged with 1.5 l of liquid propylene. 2 ml of TEA (20% strength in Varsol) were added and the mixture was stirred for 15 minutes. The catalyst system prepared above (0.897 g) was then resuspended in 20 ml of heptane and injected into the reactor and rinsed in using 15 ml of heptane. The reaction mixture was heated to the polymerization temperature of 60° C. and polymerization was carried out for one hour. The polymerization was stopped by venting the remaining propylene. The polymer was dried in a vacuum drying oven. This gave 410 g of polypropylene powder. The reactor displayed no deposits on the inner wall or stirrer. The catalyst activity was 0.46 kg of PP/g of catalyst x h.

EXAMPLE 4

Pseudo-rac-Dimethylsilanediylbis(2-methylindenyl)-zirconium Monochloride Mono(2,4-di-tert-butylphenoxide) (4)

A solution of 2.5 g (7.9 mmol) of dimethylbis(2-methylindenyl)silane in 18 ml of toluene/1 ml of THF was admixed with 5.9 ml (15.8 mmol) of a 20% strength solution of n-butyllithium in toluene and the mixture was stirred at 60° C. for 1 hour. 4.32 g (7.9 mmol) of (2) were added thereto at 20° C. and the reaction mixture was stirred at 30° C. for 1 hour. The $^1$H-NMR spectrum of a sample of the suspension showed a pseudo-rac/pseudo-meso ratio of 2:1. The reaction mixture was filtered through Celite, the filter cake was extracted with a total of 75 ml of hot toluene, the filtrate was evaporated and, after crystallization at −30° C., a yellow crystalline precipitate was isolated by filtration, washed with a little cold toluene and dried under reduced pressure. This gave 2.0 g (39%) of (4).

1H-NMR (400 MHz, CDCl$_3$): 8.03 (dd, 1H), 7.6 (dd, 1H), 7.25–7.2 (m, 2H), 7.15 (m, 1H), 7.1–7.0 (m, 2H), 6.9 (m,

1H), 6.8 (s, 1H), 6.75 (m, 1H), 6.7 (m, 1H), 6.3 (s, 1H), 5.55 (d, 1H), 2.65 (s, 3H), 2.3 (s, 3H), 1.3 (s, 3H), 1.25 (s, 9H), 1.22 (s, 3H), 1.15 (s, 9H).

COMPARATIVE EXAMPLE

Rac-Dimethylsilanediylbis(2-methylindenyl)-zirconium Dichloride

A solution of 2.5 g (7.9 mmol) of dimethylbis(2-methylindenyl)silane in 18 ml of toluene/1 ml of THF was admixed with 5.9 ml (15.8 mmol) of a 20% strength solution of n-butyllithium in toluene and the mixture was stirred at 60° C. for 1 hour. 3.0 g (7.9 mmol) of $ZrCl_4*(THF)_2$ were added thereto at 20° C., and the reaction mixture was stirred at 30° C. for 1 hour. The $^1$H-NMR spectrum of a sample of the suspension showed an rac/meso ratio of 1:1. Extraction with hot toluene and crystallization gave 0.7 g (19%) of dimethylsilanediylbis-(2-methylindenyl)zirconium dichloride.

Solubility Comparison:

50 mg of dimethylsilanediylbis(2-methylindenyl)zirconium dichloride dissolved completely in 50 ml of toluene at room temperature (solubility: about 2.1 mmol/l).

50 mg of the compound (4) dissolved immediately in <5 ml of toluene at room temperature (solubility: >15 mmol/l).

EXAMPLE 5

Pseudo-rac-Dimethylsilanediylbis(2-methyl-4,5-benzo-indenyl)zirconium Monochloride Mono(2,6-dimethyl-phenoxide) (5)

A solution of 1 g (2.4 mmol) of dimethylbis(2-methyl-4,5-benzoindenyl)silane in 7 ml of toluene/0.4 ml of THF was admixed with 1.8 ml (2.8 mmol) of a 20% strength solution of n-butyllithium in toluene and the mixture was stirred at 60° C. for 1 hour. 1.11 g (2.4 mmol) of (1) were added thereto at 20° C., and the reaction mixture was stirred at 30° C. for 1 hour. The $^1$H-NMR spectrum of a sample of the suspension showed a pseudo-rac/pseudo-meso ratio of greater than 5:1. The reaction mixture was filtered through Celite, the filter cake was extracted with a total of 55 ml of hot toluene, the filtrate was evaporated and, after crystallization at −30° C., a yellow crystalline precipitate was isolated by filtration, washed with a little cold toluene and dried under reduced pressure. This gave 0.7 g (44%) of (5).

EXAMPLE 6

Pseudo-rac-Dimethylsilanediylbis(2-methylindenyl)-zirconium Monochloride Mono(2,6-dimethylphenoxide) (6)

A solution of 1 g (3.16 mmol) of dimethylbis(2-methylindenyl)silane in 7 ml of toluene/0.4 ml of THF was admixed with 2.4 ml (6.4 mmol) of a 20% strength solution of n-butyllithium in toluene and the mixture was stirred at 60° C. for 1 hour. 1.46 g (3.15 mmol) of (1) were added thereto at 20° C., and the reaction mixture was stirred at 30° C. for 1 hour. The $^1$H-NMR spectrum of a sample of the suspension showed a pseudo-rac/pseudo-meso ratio of about 8:1. The reaction mixture was filtered through Celite, the filter cake was extracted with a total of 60 ml of hot toluene, the filtrate was evaporated and, after crystallization at −30° C., a yellow crystalline precipitate was isolated by filtration, washed with a little cold toluene and dried under reduced pressure. This gave 0.95 g (53%) of (6).

1H-NMR (400 MHz, CDCl$_3$): 7.98 (m, 1H), 7.61 (m, 1H), 7.35–7.23 (m, 2H), 7.1–6.99 (m, 3H), 6.76 (very broad s, 2H), 6.69 (s, 1H), 6.6–6.53 (m, 2H), 6.23 (s, 1H), 2.64 (s, 3H), 2.27 (s, 3H), 2.16 (br. S, 3H), 1.7 (br. s, 3H), 1.33 (s, 3H), 1.22 (s, 3H).

EXAMPLE 7

Pseudo-rac-Dimethylsilanediylbis(2-methyl-4-phenyl-indenyl)zirconium Monochloride Mono(2,6-dimethyl-phenoxide) (7)

A solution of 1 g (2.13 mmol) of dimethylbis(2-methyl-4-phenyl-indenyl)silane in 7 ml of toluene/0.4 ml of THF was admixed with 1.6 ml (4.3 mmol) of a 20% strength solution of n-butyllithium in toluene and the mixture was stirred at 60° C. for 1 hour. 1.0 g (2.16 mmol) of (1) were added thereto at 20° C., and the reaction mixture was stirred at 30° C. for 1 hour. The $^1$H-NMR spectrum of a sample of the suspension showed a pseudo-rac/pseudo-meso ratio of about 4:1. The reaction mixture was filtered through Celite, the filter cake was extracted with a total of 80 ml of hot toluene, the filtrate was evaporated and, after crystallization at −30° C., a yellow crystalline precipitate was isolated by filtration, washed with a little cold toluene and dried under reduced pressure. This gave 0.7 g (46%) of (7).

1H-NMR (400 MHz, CDCl$_3$): 8.05 (d, 1H), 7.63 (d, 1H), 7.6–6.65 (m, 18H), 6.39 (s, 1H), 2.69 (s, 3H), 2.39 (s, 3H), 1.75 (s, 3H), 1.50 (s, 3H), 1.41 (s, 3H), 1.30 (s, 3H).

COMPARATIVE EXAMPLE

Rac-Dimethylsilanediylbis(2-methyl-4-phenyl-indenyl)zirconium Dichloride

A solution of 2 g (4.26 mmol) of dimethylbis(2-methyl-4-phenyl-indenyl)silane in 14 ml of THF was admixed with 3.2 ml (8.6 mmol) of a 20% strength solution of n-butyllithium in toluene and the mixture was stirred at 50° C. for 2 hours. 1.6 g (4.6 mmol) of $ZrCl_4*(THF)_2$ were added thereto at 20° C., and the reaction mixture was stirred at 40° C. for 2 hours. The $^1$H-NMR spectrum of a sample of the suspension showed a pseudo-rac/pseudo-meso ratio of about 2:1. Most of the solvent was removed, the residue was suspended in toluene and filtered through Celite, and the filter cake was extracted with hot toluene. The filtrate was evaporated and, after crystallization at −30° C., a yellow pulverulent precipitate was isolated by filtration, washed with a little cold toluene and dried under reduced pressure. This gave 0.35 g (13%) of rac-dimethylsilanediylbis(2-methyl-4-phenylindenyl)zirconium dichloride.

EXAMPLE 8

Pseudo-rac-Dimethylsilanediylbis(2-methyl-4-(4'-tert-butylphenyl)indenyl)zirconium Monochloride Mono(2,6-dimethylphenoxide) (8)

A solution of 4 g (6.89 mmol) of dimethylbis(2-methyl-4-(4'-tert-butylphenyl)indenyl)silane in 28 ml of toluene/1.6 ml of THF was admixed with 5.14 ml (13.8 mmol) of a 20% strength solution of n-butyllithium in toluene and the mixture was stirred at 80° C. for 1 hour. 3.18 g (6.9 mmol) of (1) were added thereto at 20° C., and the reaction mixture was stirred at 30° C. for 1 hour. After addition of 25 ml of toluene, the reaction mixture was heated to 80° C. and filtered through Celite. The filter cake was extracted with a total of 150 ml of hot toluene, the filtrate was evaporated to about 20 ml and, after crystallization at 5° C., a yellow crystalline precipitate was isolated by filtration, washed with a little cold toluene and dried under reduced pressure. This gave 2.66 g (47%) of (8).

1H-NMR (400 MHz, CDCl$_3$): 7.98 (d, 1H), 7.78 (d, 1H), 7.51–6.6 (m, 11H), 6.36 (s, 1H), 2.62 (s, 3H), 2.35 (s, 3H), 1.68 (s, 3H), 1.40 (s, 3H), 1.38 (s, 3H), 1.30 (s, 9H), 1.25 (s, 3H), 1.16 (s, 9H).

We claim:

1. A process for preparing monoaryloxy-metallocenes of the formula (II), which comprises reacting a ligand starting compound of the formula (III) with a transition metal compound of the formula (I),

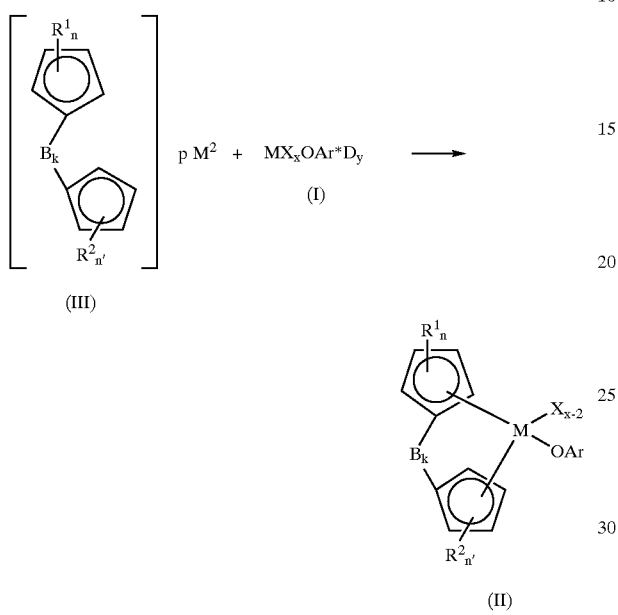

(III)

pM$^2$ + MX$_x$OAr*D$_y$ ⟶

(I)

(II)

where

M is a metal of transition group III, IV, V or VI of the Periodic Table of the Elements, x is a halogen atom, Ar is a C$_6$–C$_{40}$ aromatic group, C$_5$–C$_{24}$-heteroaryl, C$_7$–C$_{30}$-alkylaryl, fluorinated C$_6$–C$_{24}$-aryl or fluorinated C$_7$–C$_{30}$-alkylaryl, D is an uncharged Lewis base ligand, M$^2$ is Li, Na, K, MgCl, MgBr, Mg or Ca, R$^1$ are identical or different and are each Si(R$^{12}$)$_3$, where R$^{12}$ are identical or different and are each a hydrogen atom or a C$_1$–C$_{40}$ group, or R$^1$ is a C$_1$–C$_{30}$ group, or two or more radicals R$^1$ are joined to one another so that the radicals R$^1$ and the atoms of the cyclopentadienyl ring which connect them form a C$_4$–C$_{24}$ ring system which may be substituted, R$^2$ are identical or different and are each Si(R$^{12}$)$_3$, where R$^{12}$ are identical or different and are each a hydrogen atom or a C$_1$–C$_{40}$ group, or R$^2$ is a C$_1$–C$_{30}$ group, or two or more radicals R$^2$ are joined to one another so that the radicals R$^2$ and the atoms of the cyclopentadienyl ring which connect them form a C$_4$–C$_{24}$ ring system which may be substituted, x is equal to the oxidation number of M minus 1, n is from 1 to 5 when k=0, and n is from 0 to 4 when k=1, n' is from 1 to 5 when k=0, and n' is from 0 to 4 when k=1, k is zero or 1 and p is 1 for doubly positively charged metal ions or 2 for singly positively charged metal ions or metal ion fragments, y is from 0 to 2

B is a bridging structural element between the two cyclopentadienyl rings.

2. A process as claimed in claim 1 in which ansa-monoaryloxy-binsindenyl-metalocene of the formula (IV) is prepared by reacting a ligand starting compound (V) with a transition metal compound of the formula (Ia),

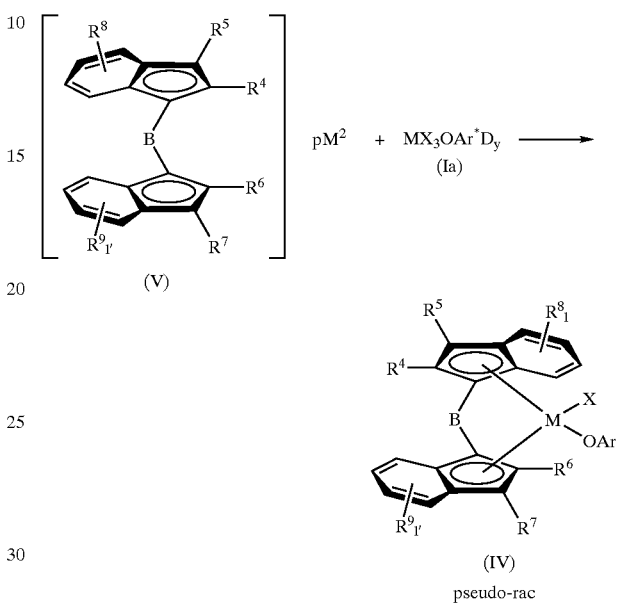

(V)

pM$^2$ + MX$_3$OAr*D$_y$ ⟶

(Ia)

(IV)

pseudo-rac where

M is Ti, Zr or Hf, x is a halogen atom,

Ar is a C$_6$–C$_{40}$ aromatic group, C$_5$–C$_{24}$-heteroaryl, C$_7$–C$_{30}$-alkylaryl, fluorinated C$_6$–C$_{24}$-aryl or fluorinated C$_7$–C$_{30}$-alkylaryl, D is an uncharged Lewis base ligand, M$^2$ is Li, Na, K, MgCl, MgBr, Mg or Ca, R$^4$, R$^6$ are identical or different and are each a hydrogen atom or a C$_1$–C$_{20}$ group, R$^5$, R$^7$ are identical or different and are each a hydrogen atom or a C$_1$–C$_{20}$ group, R$^8$ and R$^9$ are identical or different and are each a hydrogen atom, a halogen atom or a C$_1$–C$_{20}$ group, or two radicals R$^8$ or R$^9$ form a monocyclic or polycyclic ring system which may in turn be substituted, l, l' are identical or different and are each an integer from zero to 4, p is 1 for doubly positively charged metal ions or 2 for singly positively charged metal ions or metal ion fragments y is from 0 to 2 and B is a bridging structural element between the two indenyl radicals.

3. A process as claimed in claim 1, wherein M is zirconium.

4. A process as claimed in claim 1 in which a transition metal compound (Ia) of the following formula

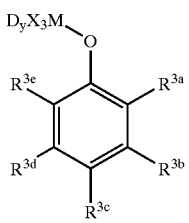

(Ia)

where

M is Ti, Zr or Hf,

X is a halogen atom,

D is an uncharged Lewis base ligand, $R^{3a}$ is halogen or $Si(R^{12})_3$, where $R^{12}$ are identical or different and are each a hydrogen atom or a $C_1$–$C_{14}$ group, or $R^{3a}$ is a $C_1$–$C_{30}$ group, $R^{3b}$ to $R^{3e}$ are identical or different and are each hydrogen, halogen or a $C_1$–$C_{30}$ group, or two or more radicals $R^{3a}$ to $R^{3e}$ may be joined to one another so that the radicals $R^3$ and the atoms of the benzene ring which connect them form a $C_4$–$C_{24}$ ring system which may in turn be substituted, and y is from 0 to 2, is used.

5. A process as claimed in claim 4, wherein

M is zirconium, x is chlorine,

D is an uncharged oxygen- or nitrogen-containing Lewis base ligand, $R^{3a}$ is halogen or a $C_1$–$C_{10}$ group, $R^{3b}$ to $R^{3e}$ are identical or different and are each hydrogen, halogen or a $C_1$–$C_{10}$ group, or two or more radicals $R^{3a}$ to $R^{3e}$ are joined to one another so that the radicals $R^3$ and the atoms of the benzene ring which connect them form a $C_4$–$C_8$ ring system which may in turn be substituted.

6. A process as claimed in claim 4, wherein

M is zirconium, x is chlorine

D is tetrahydrofuran, 1,2-dimethoxyethane or N,N,N',N'-tetramethylethylenediamine, $R^{3a}$ is chlorine, bromine or a $C_1$–$C_{10}$ group, $R^{3b}$ to $R^{3d}$ are identical or different and are each hydrogen, chlorine, bromine or a $C_1$–$C_{10}$ group, or two or more radicals $R^{3a}$ to $R^{3e}$ are joined to one another so that the radicals $R^3$ and the atoms of the benzene ring which connect them form a $C_4$–$C_6$ ring system which may in turn be substituted.

7. A process as claimed in claim 4, wherein the ratio of pseudo-rac/pseudo-meso in the crude metallocene product is greater than 1.

8. A process as claimed in claim 4, wherein the ratio of pseudo-rac/pseudo-meso is greater than 4.

9. A metallocene of the formula (IV) obtained by a process as claimed in claim 2.

10. A metallocene as claimed in claim 9 in which the zirconium fragment is zirconium monochloride
mono(2,6-dimethylphenoxide), zirconium monochloride
mono(2,4-di-tert-butylphenoxide), zirconium monochloride
mono(2-methylphenoxide), zirconium monochloride
mono(2-isopropylphenoxide), zirconium monochloride
mono(2,4-dimethylphenoxide), zirconium monochloride
mono(2,3-dimethylphenoxide), zirconium monochloride
mono(2,4,6-trimethylphenoxide), zirconium monochloride
mono(2-isopropyl-5-methylphenoxide), zirconium monochloride
mono(2-tert-butyl-6-methylphenoxide), zirconium monochloride
mono(2,6-diisopropylphenoxide), zirconium monochloride
mono(I-naphthoxide) or zirconium monochloride
mono(2-phenylphenoxide).

11. The process of claim 1 wherein

Ar is a $C_6$–$C_{14}$-aryl group substituted by $C_1$–$C_6$-alkyl and/or $C_6$–$C_{10}$-aryl radicals, D is an uncharged Lewis base ligand comprising a linear, cyclic or branched oxygen-, sulfur-, nitrogen- or phosphorus-containing hydrocarbon, $R^1$ are identical or different and are each $Si(R^{12})_3$, where $R^{12}$ are identical or different and are each a hydrogen atom or a $C_1$–$C_{20}$-alkyl, $C_1$–$C_{10}$-fluoroalkyl, $C_1$–$C_{10}$-alkoxy, $C_6$–$C_{20}$-aryl, $C_6$–$C_{10}$-fluoroaryl, $C_6$–$C_{10}$-aryloxy, $C_2$–$C_{10}$-alkenyl, $C_7$–$C_{40}$-arylalkyl, $C_7$–$C_{40}$-alkylaryl or $C_8$–$C_{40}$-arylalkenyl, or $R^1$ is a $C_1$–$C_{25}$-alkyl, $C_2$–$C_{25}$-alkenyl, $C_3$–$C_{15}$-alkylalkenyl, $C_6$–$C_{24}$-aryl, $C_5$–$C_{24}$-heteroaryl, $C_7$–$C_{30}$-arylalkyl, $C_7$–$C_{30}$-alkylaryl, fluorinated $C_1$–$C_{25}$-alkyl, fluorinated $C_6$–$C_{24}$-aryl, fluorinated $C_7$–$C_{30}$-arylalkyl or fluorinated $C_7$–$C_{30}$-alkylaryl, or two or more radicals $R^1$ are joined to one another so that the radicals $R^1$ and the atoms of the cyclopentadienyl ring which connect them form a $C_4$–$C_{24}$ ring system which may be substituted, and $R^2$ are identical or different and are each $Si(R^{12})_3$, where $R^{12}$ are identical or different and are each a hydrogen atom or a $C_1$–$C_{20}$-alkyl, $C_1$–$C_{10}$-fluoroalkyl, $C_1$–$C_{10}$-alkoxy, $C_6$–$C_{14}$-aryl, $C_6$–$C_{10}$-fluoroaryl, $C_6$–$C_{10}$-aryloxy, $C_2$–$C_{10}$-alkenyl, $C_7$–$C_{40}$-arylalkyl, $C_7$–$C_{40}$-alkylaryl or $C_5$–$C_{40}$-arylalkenyl, or $R^2$ is a $C_1$–$C_{25}$-alkyl, $C_2$–$C_{25}$-alkenyl, $C_3$–$C_{15}$-alkylalkenyl, $C_6$–$C_{24}$-aryl, $C_5$–$C_{24}$-heteroaryl, $C_7$–$C_{30}$-arylalkyl, $C_7$–$C_{30}$-alkylaryl, fluorinated $C_1$–$C_{25}$-alkyl, fluorinated $C_6$–$C_{24}$-aryl, fluorinated $C_7$–$C_{30}$-arylalkyl or fluorinated $C_7$–$C_{30}$-alkylaryl, or two or more radicals $R^2$ are joined to one another so that the radicals $R^2$ and the atoms of the cyclopentadienyl ring which connect them form a $C_4$–$C_{24}$ ring system which may be substituted.

12. The process of claim 2 wherein

Ar is a $C_6$–$C_{14}$-aryl group substituted by $C_1$–$C_6$-alkyl and/or $C_6$–$C_{10}$-aryl radicals, D is an uncharged Lewis base ligand comprising an ether, polyether, amine or polyamine, $R^4$, $R^6$ are identical or different and are each a hydrogen atom or a $C_1$–$C_{18}$-alkyl, $C_2$–$C_{10}$-alkenyl, $C_3$–$C_{15}$-alkylalkenyl, $C_6$–$C_{18}$-aryl, $C_5$–$C_{18}$-heteroaryl, $C_7$–$C_{20}$-arylalkyl, $C_7$–$C_{20}$-alkylaryl, fluorinated $C_1$–$C_{12}$-alkyl, fluorinated $C_6$–$C_{18}$-aryl, fluorinated $C_7$–$C_{20}$-arylalkyl or fluorinated $C_7$–$C_{20}$-alkylaryl, $R^5$, $R^7$ are identical or different and are each a hydrogen atom or a $C_1$–$C_{18}$-alkyl, $C_2$–$C_{10}$-alkenyl, $C_3$–$C_{15}$-alkylalkenyl, $C_6$–$C_{18}$-aryl, $C_5$–$C_{18}$-heteroaryl, $C_7$–$C_{20}$-arylalkyl, $C_7$–$C_{20}$-alkylaryl fluorinated $C_1$–$C_{12}$-alkyl, fluorinated $C_6$–$C_{18}$-aryl, fluorinated $C_7$–$C_{20}$-arylalkyl or fluorinated $C_7$–$C_{20}$-alkylaryl, $R^8$ and $R^9$ are identical or different and are each a hydrogen atom, a halogen atom or a linear or branched $C_1$–$C_{18}$-alkyl group, $C_2$–$C_{10}$-alkenyl, $C_3$–$C_{15}$-alkylalkenyl, a substituted or unsubstituted $C_6$–$C_{15}$-aryl group, $C_6$–$C_{18}$-heteroaryl, $C_7$–$C_{20}$-arylalkyl, $C_7$–$C_{20}$-alkylaryl, fluorinated $C_1$–$C_{12}$-alkyl, fluorinated $C_6$–$C_{18}$-aryl, fluorinated $C_7$–$C_{20}$-arylalkyl or fluorinated $C_7$–$C_{20}$-alkylaryl or two radicals $R^8$ or $R^9$ form a monocyclic or polycyclic ring system which may in turn be substituted, and l, l' are identical or different and are each an integer of 1 or 2.

13. The process of claim 4 wherein

M is Ti, Zr or Hf,

X is a halogen atom,

D is an uncharged Lewis base ligand, comprising a linear, cyclic or branched oxygen-, sulfur-, nitrogen- or phosphorus-containing hydrocarbon, $R^{3a}$ is halogen or $Si(R^{12})_3$, where $R^{12}$ are identical or different and are each a hydrogen atom or a $C_1$–$C_4$-alkyl, $C_1$–$C_4$-alkoxy, $C_6$–$C_{10}$-aryl, $C_6$–$C_{10}$-fluoroaryl, $C_6$–$C_{10}$-aryloxy, $C_2$–$C_{10}$-alkenyl, $C_7$–$C_{14}$-arylalkyl or $C_7$–$C_{14}$-alkylaryl, or $R^{3a}$ is a $C_1$–$C_{25}$-alkyl, $C_2$–$C_{25}$-alkenyl, $C_3$–$C0_5$-alkylalkenyl, $C_6$–$C_{24}$-aryl, $C_5$–$C_{24}$-heteroaryl, $C_1$–$C_{10}$-alkyloxy, $C_6$–$C_{10}$-aryloxy, $C_7$–$C_{30}$-arylalkyl, $C_7$–$C_{30}$-alkylaryl, fluorinated $C_1$–$C_{25}$-alkyl, fluorinated $C_6$–$C_{24}$-aryl, fluorinated $C_7$–$C_{30}$-arylalkyl or fluorinated $C_7$–$C_{30}$-alkylaryl, and $R^{3b}$ to $R^{3e}$ are identical or different and are each hydrogen, halogen or a $C_1$–$C_{25}$-alkyl, $C_2$–$C_{25}$-alkenyl, $C_3$–$C_{15}$-alkylalkenyl, $C_6$–$C_{24}$-aryl, $C_5$–$C_{24}$-heteroaryl, $C_1$–$C_{10}$-alkyloxy, $C_6$–$C_{10}$-aryloxy, $C_7$–$C_{30}$-arylalkyl, $C_7$–$C_{30}$-alkylaryl, fluorinated $C_1$–$C_{25}$-alkyl, fluorinated $C_6$–$C_{24}$-aryl, fluorinated $C_7$–$C_{30}$-arylalkyl or fluorinated $C_7$–$C_{30}$-alkylaryl, or two or more radicals $R^{3a}$ to $R^{3e}$ may be joined to one another so that the radicals $R^3$ and the atoms of the benzene ring which connect them form a $C_4$–$C_{24}$ ring system which may in turn be substituted.

14. The process of claim 4 wherein

M is zirconium, x is chlorine,

D is an uncharged oxygen- or nitrogen-containing Lewis base ligand, comprising an ether, polyether, amine or polyamine, $R^{3a}$ is halogen or a $C_1$–$C_8$-alkyl, $C_2$–$C_8$-alkenyl, $C_3$–$C_8$-alkylalkenyl, $C_6$–$C_{10}$-aryl, $C_5$–$C_9$-heteroaryl, $C_1$–$C_4$-alkyloxy, $C_6$-aryloxy, $C_7$–$C_{10}$-arylalkyl, $C_7$–$C_{10}$-alkylaryl, $R^{3b}$ to $R^{3e}$ are identical or different and are each hydrogen, halogen or a $C_1$–$C_8$-alkyl, $C_2$–$C_8$-alkenyl, $C_3$–$C_8$-alkylalkenyl, $C_6$–$C_{10}$-aryl, $C_5$–$C_9$-heteroaryl, $C_1$–$C_4$-alkyloxy, $C_6$-aryloxy, $C_7$–$C_{10}$-arylalkyl, $C_7$–$C_{10}$-alkylaryl, or two or more radicals $R^{3a}$ to $R^{3e}$ are joined to one another so that the radicals $R^3$ and the atoms of the benzene ring which connect them form a $C_4$–$C_8$ ring system which may in turn be substituted.

* * * * *

UNITED STATES PATENT AND TRADEMARK OFFICE
CERTIFICATE OF CORRECTION

PATENT NO. : 6,620,953 B1
DATED : September 16, 2003
INVENTOR(S) : Bingel et al.

It is certified that error appears in the above-identified patent and that said Letters Patent is hereby corrected as shown below:

<u>Column 36,</u>
Line 31, add claim 15 as follows:

15. The process of claim 4 wherein
   M is zirconium,
   x is chlorine
   D is tetrahydrofuran, 1,2-dimethoxyethane or N,N,N',N'-tetramethylethylenediamine,
   $R^{3a}$ is chlorine, bromine or a $C_1$-$C_6$-alkyl, $C_2$-$C_4$-alkenyl, $C_6$-$C_{10}$-aryl, and
   $R^{3b}$ to $R^{3d}$ are identical or different and are each hydrogen, chlorine, bromine or a $C_1$-$C_6$-alkyl, $C_2$-$C_4$-alkenyl, $C_6$-$C_{10}$-aryl, or two or more radicals $R^{3a}$ to $R^{3e}$ are joined to one another so that the radicals $R^3$ and the atoms of the benzene ring which connect them form a $C_4$-$C_6$ ring system which may in turn be substituted.

Signed and Sealed this

Thirteenth Day of January, 2004

JON W. DUDAS
*Acting Director of the United States Patent and Trademark Office*